(12) United States Patent
Platteborze et al.

(10) Patent No.: US 7,790,181 B2
(45) Date of Patent: Sep. 7, 2010

(54) LIVE ATTENUATED VIRAL VACCINES FOR EASTERN EQUINE ENCEPHALITIS VIRUS

(75) Inventors: Peter L. Platteborze, Bel Air, MD (US); Michael D. Parker, Frederick, MD (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 781 days.

(21) Appl. No.: 10/853,952

(22) Filed: May 26, 2004

(65) Prior Publication Data

US 2004/0253271 A1 Dec. 16, 2004

Related U.S. Application Data

(60) Provisional application No. 60/474,752, filed on May 29, 2003.

(51) Int. Cl.
*A61K 39/12* (2006.01)
*C12N 7/04* (2006.01)
*C12N 15/40* (2006.01)

(52) U.S. Cl. ............... 424/218.1; 424/205.1; 424/204.1; 424/93.2; 424/235.1; 435/235.1; 435/236

(58) Field of Classification Search .................. None
See application file for complete search history.

(56) References Cited

U.S. PATENT DOCUMENTS

| | | | | |
|---|---|---|---|---|
| 5,505,947 | A | 4/1996 | Johnston et al. | 424/218.1 |
| 5,792,462 | A | 8/1998 | Johnston et al. | 424/199.1 |
| 6,156,558 | A | 12/2000 | Johnston et al. | 435/235.1 |
| 6,261,567 | B1 | 7/2001 | Hart | |
| 6,261,570 | B1 * | 7/2001 | Parker et al. | 424/205.1 |
| 6,296,854 | B1 | 10/2001 | Pushko et al. | 424/218.1 |

FOREIGN PATENT DOCUMENTS

| | | |
|---|---|---|
| WO | WO 98/53077 | 11/1998 |
| WO | WO98/53077 A | 11/1998 |

OTHER PUBLICATIONS

Genbank: accession No. U01034. Deposited: Mar. 2, 2000. Author: Weaver.*
Mitchell et al (1992) Science. 257(5069): 526-7.*
Brault et al (1999) Am J Trop Med Hyg. 61(4): 579-86.*
Berman et al. A Safety Test for Eastern Equine Encephalomyelitis Vaccine. Applied Microbiology. 1967. vol. 15, No. 4. p. 968-969.*
Schoepp, Randal, et al., "REcombinant chimeric western and eastern equine encephalitis viruses as potential vaccine candidates", Virology, vol. 302, No. 2, Oct. 25, 2002.
Database EMBL [online] "Eastern equine encephalomyelitis virus North AMerican antigenic variety nonstrucutal polyprotein and structural polyprotein genes, complete cds." XP002307427, Nov. 21, 1993.
Davis, et al., "Attenuated mutants of Venezuelan equine encephalitis virus containing lethal mutations in the PE2 cleavage signal combined with a second site suppressor mutation in E1", Virology, vol. 212, No. 1, 1995, pp. 102-110.
Mitchell, e tal., "Isolation of eastern Equine Encephalitis Virus From Aedes-Albopictus in Florida", Sciendce, vol. 257, No. 5069, 1992, pp. 536-527.
Schoepp, et al. "Recombinant chimeric western and eastern equine encephalitis viruses as potential vaccine candidates", Virology, vol. 302, No. 2, Oct. 25, 2002, pp. 299-309.
Database embl Online!, Nov. 21, 1993, "Eastern Equine encephalomyelitis virus North American antigenic variety nonstructural polyprotein and structural polyprotein genes, complete cds." XPOO2307427 retrieved retrieved from EBI accession No. EM_PRO: TOGU01034, database accession No. TOBU01034, the whole document.
Davis, e tal.: "Attenuated mutants of Venezuelan equine encephalitis virus containing lethal mutations in the PE2 cleavage signal combined with a second site suppressor mutation in E1", Virology, vol. 212, No. 1, 1995, pp. 102-110.
Mitchell, et al.: "Isolation of Eastern Equine Encephalitis Virus From Aedes-Albopictus in Florida", Science (Washington DC), vol. 257, No. 5069, 1992, pp. 526-527.

* cited by examiner

*Primary Examiner*—Zachariah Lucas
*Assistant Examiner*—Michelle Horning
(74) *Attorney, Agent, or Firm*—Elizabeth Arwine

(57) ABSTRACT

Live attenuated Eastern Equine Encephalitis (EEE) vaccines that outperform the PE-6 vaccine in mice aerosol challenged with >1,000×LD50. Candidates include four furin-cleavage deletion mutants and one E3 deletion mutant. Each vaccine provided protection in birds against antigenically distinct North and South American strains of EEE. The PE-6 vaccine does not provide protection against South American EEEs. Animals inoculated with each of the vaccines of the invention developed neutralizing antibodies to EEE.

18 Claims, 13 Drawing Sheets

Assembly of Eastern Equine Encephalitis full-length infectious clone pEE2002.

```
        Stu I 1534      NcoI 4435          ClaI 7204              Not I 11681+
           |               |                  |                        |
           |               |                  |                        |———E3' Not I
  Nsp-15——→                                   |          E6956F——→
ET7C——→        ←——E1645R  E4360F——→    ←——E4791R            ←——E7377R
```

Oligonucleotide Primers Utilized in Construction of pEE2002, pEE2202 & pEE4202

| | |
|---|---|
| Nsp-15 | CCTTAAAGGCCTTCAGGATGAAGCTGA |
| E4791R | GGGGGGAAGAGGCTTCCGAC |
| ET7C | GACTGAATTCAGATCTGTTAATACGACTCACTATAGAGATAGGGTACGGTGTAGA |
| E1645R | GCCTGCTCCTGCCCTCTGC |
| E4360F | CGCAGGTGGTAAGGACAGGG |
| E6956F | CACTTACACCCGATTTAAGTTCG |
| E7377R | GTGATGCCAATTCTGTTCC |
| E3' Not I | TAATATTTCAAAAAAAAAAAAAAAAAAAAAAAAAGGCCGC |
| [Furin cleavage deletion] EEE F1 d5R | TGAAATGAGTGTCCAAATCAGCATTACATTTCACAGC |
| [Furin cleavage deletion] EEE F1 d5F | GCTGTGAAATGTAATGCTGATTTGGACACTCATTTCA |
| E8275F | GTCCTGGGTGGAGTCAACG |

Fig. 1A

Organization and Expression of the EEE Virus Genome

Nonstructural Proteins | Structural Proteins

↑ Translation

5' CAP — nsP1 nsP2 nsP3 nsP4 ————— $A_n$ 3'  (+)

$U_n$ Replication (−)

↓ Transcription

CAP — $A_n$  (+)

26 S mRNA

↓ Translation of Structural Proteins

| Capsid | PE2 | 6K | E1 |

PE2 — E1

Heterodimers form in ER, transported to Golgi

↓ Furin

E3 | RRTRR — E2 — E1

PE2 is cleaved; heterodimer reaches cell membrane

EEE virion glycoprotein spike comprised of three E2-E1 heterodimers. E3?

Fig. 3

Strategy for the Construction of a Genetically Engineered EEE Vaccine

Identification of attenuating mutations:
- sequence of attenuated variants
- mutagenesis of conserved sequences

EEE e.g., pE4002

T7 pBR322

Wild type, full length cDNA clone

Site directed mutagenesis e.g., pE4202.X

Molecularly defined clone with attenuating mutations

RNA

Virus Rescue

Testing in animal models

IND Submission (FDA)

Fig. 5

Example 2 EEE Mutations
Small Plaque (SP) RPE.40-derived Mutant EEE

Fig. 6

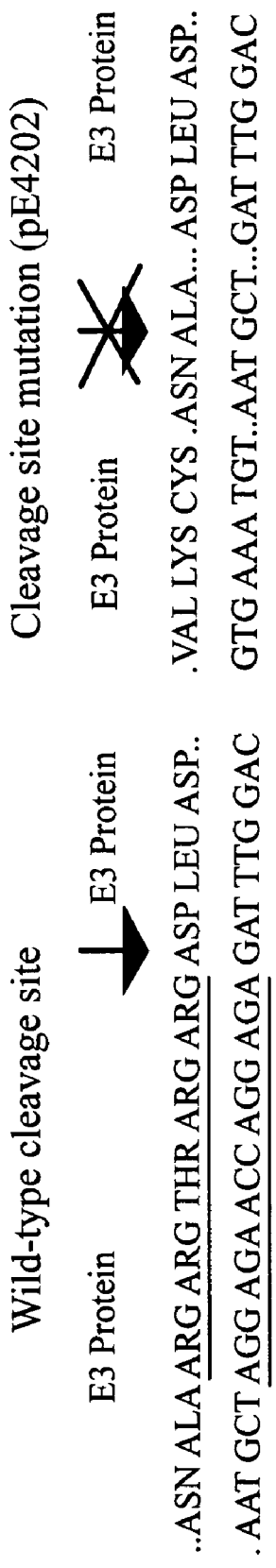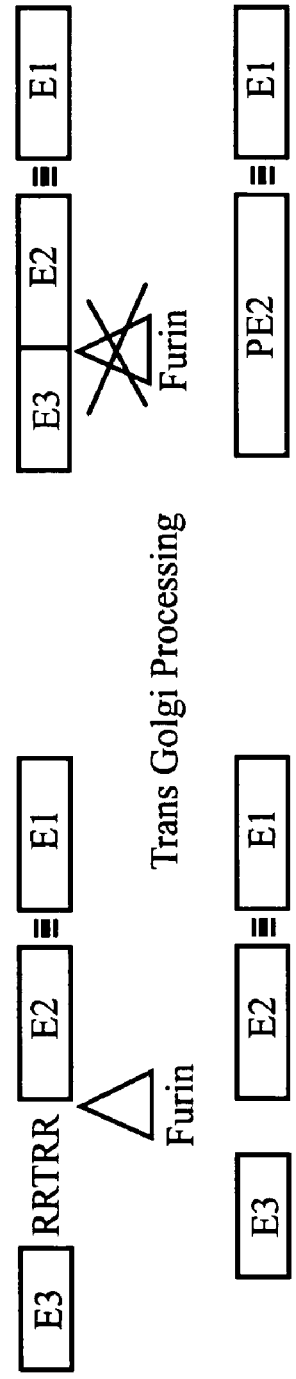
Fig. 8

Serial Passage of pEE4202 Mutant EEE

| Serial Passage # | BHK Titer | RPE.40 Titer |
|---|---|---|
| Transfection | 1.0E4 | 1.0E4 |
| Pass 2 | 3.3E4 | 5.2E5 |
| Pass 3 | 4.2E3 | 1.0E7 |
| Pass 4 | 1.0E5 | 2.7E7 |
| Pass 5 | 1.0E6 | 1.2E7 |
| Pass 6 | 1.1E7 | 9.0E7 |

Fig. 9

Example 4 Mutant EEEs
[Pt 1 of 2]

Fig. 10

Example 4 Mutant EEEs
[Pt2 of 2]

Fig. 11

SEQUENCE LISTING

<160> NUMBER OF SEQ ID NOS: 19

<210> SEQ ID NO 1
<211> LENGTH: 11775
<212> TYPE: DNA
<213> ORGANISM: Eastern equine encephalomyelitis virus

<400> SEQUENCE: 1
atagggtacg gtgtagaggc aaccaccccta tttccaccta tccaaaatgg agaaagttca      60
tgttgactta gacgcagaca gcccattcgt caagtcactg caaagatgct ttccacattt     120
tgagatagaa gcaacgcagg tcactgacaa tgaccatgct aatgctaggg cgttttcgca     180
cctagctact aagctcattg agggagaagt ggatacagac caggtgatcc tggatattgg     240
gagcgcgcct gtaaggcaca cgcattccaa acataagtac cactgtattt gcccaatgaa     300
gagcgcagaa gaccctgaca gactctaccg ctacgcagac aagcttagaa agagtgatgt     360
cactgacaaa tgtattgcct ctaaggccgc ggacctgcta acagtaatgt cgacgcccga     420
cgctgagaca ccctcgttat gcatgcacac tgactcaact tgcaggtacc acggctccgt     480
ggccgtatat caggatgtat atgcagtgca tgcaccgact tccatttact accaggcgct     540
gaaaggtgta cgaactatct attggatcgg gttcgatact acaccgttca tgtataagaa     600

```
catggcaggc gcctacccta catacaacac taattgggcc gatgaaagtg tgttggaagc      660
cagaaatata gggctgggta gttcagactt gcacgaaaag agtttcggaa aagtatccat      720
tatgaggaag aagaaattac aacccaccaa taaagtaata tttctgtgg ggtcaactat       780 ttatactgaa gagagaatac tgttacgcag ttggcatcta cctaatgttt ttcatctaaa      840
aggtaaaact agctttacag gcagatgtaa cactatcgtc agctgcgaag gttacgttgt      900
caagaagatt acgcttagtc ctgggattta cgggaaagtg gataatcttg cttcgaccat      960
gcaccgagag ggattcttaa gttgcaaggt tacagatacg ttaagagggg agagggtctc     1020 tttcccgtg tgtacgtacg tgccagcgac actgtgcgac cagatgaccg ggatactggc      1080
gactgacgtc agtgtcgatg acgcccagaa gctgctggtt gggctcaacc agcgaattgt     1140
cgtcaatggc agaacacaac gtaacacaaa taccatgcag aattatctat taccagtggt     1200
cgcccaggcg ttctcgcggt gggcgcggga acaccgcgca gacctggagg acgaaaaagg     1260 gctagggta cgggaacgtt ccctagtcat gggctgctgc tgggctttca aaactcacaa      1320
gatcacatcc atttacaaga gacctgggac tcaaactatc aagaaggtgc cgccgtatt      1380 caattccttt gtcatcccac aaccaaccag ctatgggctt gatataggat tgcgtcgccg     1440
aattaagatg ctattcgacg caaagaaggc acccgctcca attattactg aggccgacgt     1500
tgcacacctt aaaggcctgc aggatgaagc tgaagccgtg gctgaggctg aagccgtacg     1560
tgcagcacta cctccacttc tgccggaggt cgacaaggag accgtagagg ctgacatcga     1620
cctgatcatg caggaggcag gagcaggcag cgtggagaca cctagacgac acatcaaggt     1680
cacgacgtac ccaggagaag aaatgatcgg ctcgtacgca gtgctttcac cacaagcggt     1740
ccttaacagc gagaagctcg cttgtattca cccgttagct gagcaagtgc tcgtgatgac     1800
tcacaaaggg cgcgcaggac gatacaaggt agagccatac cacggtagag ttatcgtccc     1860
tagtggtaca gctataccaa tcctcgattt ccaggctctg agtgaaagtg caaccatagt     1920
atttaacgaa cgggagttcg ttaaccgtta cttacaccac attgccgtta acggaggggc     1980
actgaataca gatgaagagt actacaaggt tgtgaaaagc actgagacag actctgagta     2040
cgtatttgac atcgacgcaa agaagtgcgt aaagaaaggg gatgccggac caatgtgcct     2100
ggtcggcgaa ttagtagacc cgccattcca cgaatttgcg tacgagagtt taaaaacacg     2160
tcctgctgca ccacacaaag tgcctaccat cggagtttat ggagtcccag gttccggaaa     2220
gtctggtata atcaaaagcg ctgttaccaa acgtgatctg gtggtcagtg caaagaaaga     2280
aaattgcatg gaaatcatta agacgtcaa acgtatgcgc ggcatggaca tcgccgcccg     2340
cacagtggat tcggtgctgc taaatggggt aaaacactcc gtcgacacac tgtacataga     2400
cgaggcattc gcttgccatg cagggaccct gctagcactt attgccatcg tcaagccaaa     2460
gaaagttgta ttgtgtggag atccgaaaca atgcggcttc tttaacatga tgtgtctaaa     2520 agtgcattt aaccacgaga tatgcacaga agtgtatcac aagagtattt ctcggcgatg      2580
cactaagaca gtgacatcca tcgtttccac cctgttctat gataaacgga tgagaactgt     2640
caacccatgc aatgataaga tcataataga taccaccagt actaccaaac ctttaaagga     2700
tgacataata ttaacctgct ttagagggtg ggttaaacaa ctgcagattg actacaagaa     2760
ccacgagatc atgactgcag cggcctcaca ggggcttact agaaaagggg tatacgcagt     2820
gcgctacaag gtcaatgaga acccactata cgcacagaca tctgagcatg tgaatgtatt     2880
acttacacgc actgaaaaac gtatagtatg gaagactttg gccggtgacc cttggatcaa     2940
gacgttgaca gcatcgtatc cgggtaattt caccgccaca ctggaagaat ggcaagctga     3000
```

```
gcatgacgct atcatggcga aaatacttga dacaccagct agcagcgacg ttttccaaaa    3060
taaagtgaac gtctgctggg ccaaagcgct agaacctgtg ttggccaccg ccaatattac    3120
gctgacccgc tcgcagtggg agactattcc agcgttcaag gatgacaaag cgtattcgcc    3180
tgagatggcc ttaaactttt tctgcaccag attctttggc gtcgacatcg acagcgggtt    3240
gttctccgcg ccaactgttc cgctgactta caccaatgaa cactgggata atagcccagg    3300
tccaaacatg tatggtttgt gcatgcgcac tgctaaagaa cttgcacgtc ggtatccttg    3360
tattctgaaa gccgtggata caggtagagt ggctgacgtt cgcacagaca ctatcaaaga    3420
ctataacccg ctaataaatg tggtaccctt gaatagaaga ctcccacact cattggttgt    3480
cacacataga tacactggga acggtgatta ctcccagcta gtgaccaaga tgaccggaaa    3540
aaccgtacta gtagtgggta cacctatgaa cataccagga aagagagtcg agacactagg    3600
cccaagccca caatgtacat ataaagcgga actggacctg gcattcctg ccgctttagg     3660
caaatatgac atcatttta ttaacgtgag gactccctac cgacaccacc attaccaaca     3720
gtgcgaggac catgcgatcc accacagcat gcttaccaga aaagcagtgg accatttgaa    3780
caaaggcggt acgtgcatcg cattgggcta tgggactgcg gacagagcca ccgagaacat    3840
tatctctgca gtcgcccgct cattcaggtt ctcacgtgtg tgccagccga agtgtgcctg    3900
ggaaaacact gaggtcgcgt tcgtgttttt cggcaaggac aacggcaacc atctccaaga    3960
tcaagacagg ctgagtgttg tgttaaacaa catataccaa gggtcaactc aacatgaagc    4020
tggcagagca cctgcgtata gagtggtgcg cggtgacata acaaagagca atgatgaggt    4080
tattgttaac gcggcgaaca acaaagggca acccggtagc ggtgtgtgtg gcgcccttta    4140
caggaagtgg cctggagctt ttgataagca gccggtagca actggtaaag cgcacctcgt    4200
caagcattct ccgaacgtca tccatgccgt tggccctaat tttctcggc tatcagaaaa     4260
cgaaggagac cagaaattgt ctgaagtgta catggacatt gccagaatta tcaacaacga    4320
gaggtttact aaagtctcca ttccgttgtt atctaccggc atctacgcag gtaaagga      4380
cagggttatg caatcgctga accatttatt tacagccatg gatactaccg acgcagacat    4440
tactatttac tgtctagata agcaatggga gtcaagaata aaggaagcta tcactcggaa    4500
ggaaagcgtt gaagagctta ctgaggatga cagaccagtt gacattgaac tggtacgggt    4560
gcacccgttg agcagcttgg caggtagacc tggttattca accaccgagg caaggtgta    4620
ttcgtaccta gagggactaggtttcatca aactgccaaa dacatagctg aaatttacgc       4680
tatgtggcct aacaagcaag aagcaaacga gcagatttgc ttatacgtgt gggagagag     4740
tatgaacagc atccgctcta agtgtccagt tgaagagtcg gaggcctctt ccccccctca    4800
caccatcccg tgtctgtgca actatgcaat gactgcagag cgagtttaca gattacgtat    4860
ggcaaagaat gaacaattcg cagtttgttc gtcctttcag ttaccgaaat acaggattac    4920
aggggttcag aaaattcaat gcagtaaacc tgtgatattc tctggcactg tacccccggc    4980
catacatcca agaaaattcg catctgtgac agtggaagac actccggtgg tccaacctga    5040
aaggttggtg cctaggcgac ctgcaccgcc tgtgcccgta cctgcaagaa tccccagccc    5100
tccatgtaca tcgaccaacg gatcgacgac cagtatacaa tcactggggg aggatcaaag    5160
cgcatctgct tctagcggag ctgaaatctc tgtagaccag gtttcgctat ggagcatacc    5220
cagcgctact gggttcgatg tgcgtacctc ctcatcgttg agtctagagc agcctacctt    5280
tccgacaatg gttgtcgaag cagagattca cgccagtcaa ggatcactgt ggagcatacc    5340
```

```
cagtatcacc ggatctgaaa cccgtgctcc gtcacctcca agtcaggata gtagaccttc    5400 cacccccatct gcaagtggtt cacacacgtc cgtggactta atcacgtttg acagcgttgc   5460
agagattttg gaggatttca gtcgttcgcc gtttcaattt ttgtctgaaa tcaaacctat    5520
tcctgcacct cgtacccgag ttaataacat gagccgcagc gcagacacga tcaaaccaat   5580
tccaaagccg cgtaaatgcc aggtgaagta cacgcagcca cctggcgtcg ccagggtcat    5640
atcggcagcg gaatttgacg agtttgtgcg gaggcactcg aattgacggt acgaagcggg    5700
cgcgtacatt ttctcatccg agacgggaca agggcacctg caacaaaaat ctacgcggca    5760
atgcaaactc cagtatccaa tcctggagcg ttccgtccat gagaaatttt acgcccgcg     5820 cctcgatctc gagcgtgaga agctgttgca gaagaaacta caattgtgtg cttctgaagg    5880
taatcggagc aggtatcagt ctcgtaaagt agagaacatg aaggcaatca ccgttgagcg    5940
tctactgcag gggataggct catacctctc tgcagaaccg caaccagttg aatgctacaa    6000
agtcacctat cctgctccca tgtattcaag tactgcaagc aacagctttt catcagcaga    6060
agtggccgtc aaagtctgca acctagtact gcaagagaat tttcccaccg tagccagcta    6120
taacataacg gatgagtatg atgcctatct tgatatggtg gacggagcat cctgctgttt    6180
agatactgcc acctttgcc cagccaaatt aaggagcttt ccaaagaagc acagttattt     6240
gcggcctgag atacgatcag cagtgccatc accgattcaa aacacgctcc agaatgtact    6300
agcagcagcc acgaaacgga attgcaatgt cactcaaatg agggaacttc cagtgttgga    6360
ttcagctgcc ttcaacgtgg agtgtttcaa aaagtacgcc tgtaacgatg agtactggga    6420
cttctacaag acaaacccga taagactcac cgcagaaaat gttactcagt atgttactaa    6480
gttaaaggga cccaaagcag ctgcccttt tgcgaaaacg cataacttac agccattgca    6540
tgagatacca atggatagat tcgtgatgga ccttaaacgg gatgtcaagg ttacacccgg    6600
gacaaaacat actgaagaaa gaccaaaagt tcaggtgata caggcagctg atccacttgc    6660
aaccgcctac ctatgtggta tacatcgaga gcttgtgcgc aggttgaacg cagtgctgct    6720
accgaacatc cacactttgt ttgacatgtc tgcagaagat tttgatgcta tcattgccga    6780
acactttcaa ttcggcgacg cggtgttaga gacagacata gcttcttttg ataaaagcga    6840
ggacgatgct atcgccatgt ctgctctaat gattcttgaa gacctaggag ttgatcaggc    6900
actgttaaac ctaattgaag cagcctttgg gaacataaca tctgtgcact taccaacagg    6960
cacccgattt aagttcgggg caatgatgaa atccgggatg tttttgacac tctttattaa    7020
tactgttgtc aatatcatga tcgctagccg cgtgctccgc gagcggttga ccacttcccc    7080
ctgcgcagca tttatcggcg acgacaacat cgtgaaaggg gttacatctg acgcgctgat    7140
ggcagagcgg tgcgccacgt ggttgaacat ggaagtgaag atcatcgatg cagtagtcgg    7200
agtaaaggca ccgtacttt gcggagggtt catcgtagtc gatcagatca caggaactgc     7260
gtgcagagtc gccgaccccc tgaagagact gtttaagcta ggtaagccgc ttccactgga    7320
cgatgaccaa gacgtcgaca ggcgcagagc tctgcatgat gaagcggcac gttggaacag    7380
aattggcatc actgaagagc tggtgaaagc agttgaatca cgctacgagg tgaactacgt    7440
gtcactaatc atcacagcgt tgactacatt agcatcttca gttagcaact ttaaacacat    7500
aagaggtcac cccataaccc tctacggctg acctaaatag gttgtgcatt agtacctaac    7560
ctatttatat tatattgcta tctaaatatc agagatgttc ccatacccta cacttaacta    7620
cccgcctatg cgccgattaa acccgatggc ctaccgggat cctaatccgc ctaggcgcag    7680
gtggcggccc tttaggccac cacttgcagc tcaaattgag gacctgagac gttccattgc    7740
```

```
taacctgact ttgaaacaac gagcacctaa ccctccagca ggaccgcccg ccaaacgcaa    7800
gaagcctgcg cccaagccta agcctgcgca ggcgaaaaag aagcgaccac caccacctgc    7860
caagaaacaa aaacgtaaac ctaaaccagg caaacgacag cgaatgtgta tgaagctaga    7920
gtcagataaa acgtttccga tcatgttgaa cggacaggtg aatggttacg cgtgcgtcgt    7980
gggtggacga gtgtttaaac cgctgcacgt agaaggcaga atagacaacg agcaactggc    8040
cgctatcaag ctgaagaagg ccagcatata tgaccttgag tacggtgatg tgccacaatg    8100
catgaaatca gataccctcc agtacaccag tgacaagcct cctggctttt ataactggca    8160
tcatggagct gtgcagtatg agaacaacag gttcaccgta ccacgagggg tcggtggaaa    8220
gggcgacagc gggagaccta ttcttgacaa caaaggtaga gtcgtcgcaa ttgtcctggg    8280
tggagtcaac gaaggatcca ggacggctct atcagtggtg acatggaacc aaaaggggt    8340
tacagtcaaa gatacaccag aggggtcaga gccatggtcg ctcgccactg ttatgtgcgt    8400
cctggccaat atcacgtttc catgtgatca accaccctgc atgccatgct gttatgaaaa    8460
gaatccacac gaaacactca ccatgctgga acagaattac gacagccgag cctatgatca    8520
gctgctcgat gccgctgtga atgtaatgc taggagaacc aggagagatt tggacactca    8580
tttcacccag tataagttgg cacgcccgta tattgctgat tgccctaact gtgggcatag    8640
tcggtgcgac agccctatag ctatagaaga agtcagaggg gatgcgcatg caggagtcat    8700
ccgcatccag acatcagcta tgttcggtct gaagacggat ggagtcgatt tggcctacat    8760
gagtttcatg aacggcaaaa cgcagaaatc aataaagatc gacaacctgc atgtgcgcac    8820
ctcagcccct tgttccctcg tgtcgcacca cggctattac atcttggctc aatgcccacc    8880
aggggacacg gttacagttg gtttcacga cgggcctaac cgccatacgt gcacagttgc    8940
ccataaggta gaattcaggc cagtgggtag agagaaatac cgtcacccac ctgaacatgg    9000
agttgaacta ccgtgtaacc gttacactca caagcgtgca gaccaaggac actatgttga    9060
gatgcatcaa ccagggctag ttgccgacca ctctctcctt agcatccaca gtgccaaggt    9120
gaaaattacg gtaccgagcg cgcccaagt gaaatactac tgcaagtgtc cagatgtacg    9180
agagggaatt accagcagcg accatacaac cacctgcacg gatgtcaaac aatgcagggc    9240
ttacctgatt gacaacaaga aatgggtgta caactctgga agactgcctc gaggagaggg    9300
cgacactttt aaaggaaaac ttcatgtgcc ctttgtgcct gttaaggcca agtgcatcgc    9360
cacgctggca ccggagcctc tagttgagca caaacaccgc accctgattt tacacctgca    9420
cccggaccat ccgaccttgc tgacgaccag gtcacttgga agtgatgcaa atccaactcg    9480
acaatggatt gagcgaccaa caactgtcaa tttcacagtc accggagaag ggttggagta    9540
tacctgggga aaccatccac caaaaagagt atgggctcaa gagtcaggag aagggaaccc    9600
acatggatgg ccgcacgaag tggtagtcta ttactacaac agataccctg taaccacaat    9660
tatcgggtta tgcacctgtg tggctatcat catggtctct tgtgtcacat ccgtgtggct    9720
cctttgcagg actcgcaatc tttgcataac cccgtataaa ctagcccga acgctcaagt    9780
cccaatactc ctggcgttac tttgctgcat taagccgacg agggcagacg acaccttgca    9840
agtgctgaat tatctgtgga acaacaatca aaactttttc tggatgcaga cgcttatccc    9900
acttgcagcg cttatcgtat gcatgcgcat gctgcgctgc ttattttgct gtgggccggc    9960
ttttttactt gtctgcggcg ccttgggcgc cgcagcgtac gaacacacag cagtgatgcc    10020
gaacaaggtg gggatcccgt ataaagcttt agtcgaacgc ccaggttatg cacccgttca    10080
```

-continued

```
tctacagata cagctggtta ataccaggat aattccatca actaacctgg agtacatcac    10140
ctgcaagtac aagacaaaag tgccgtctcc agtagtgaaa tgctgcggtg ccactcaatg    10200
tacctccaaa ccccatcctg actatcagtg tcaggtgttt acaggtgttt acccattcat    10260
gtggggagga gcctactgct tctgcgacac cgaaaacacc cagatgagcg aggcgtatgt    10320
agagcgctcg gaagagtgct ctatcgacca cgcaaaagct tataaagtac acacaggcac    10380
tgttcaggca atggtgaaca taacttatgg gagcgtcagc tggagatctg cagatgtcta    10440
cgtcaatggt gaaactcccg cgaaaatagg agatgccaaa ctcatcatag gtccactgtc    10500
atctgcgtgg tccccattcg ataacaaggt ggtggtttat gggcatgaag tgtataatta    10560
cgactttcct gagtacggca ccggcaaagc aggctctttt ggagacctgc aatcacgcac    10620
atcaaccagc aacgatctgt acgcaaacac caacttgaag ctacaacgac ccaggctgg    10680 tatcgtgcac acacctttca cccaggcgcc ctctggcttc gaacgatgga aagggacaa    10740 aggggcaccg ttgaacgacg tagccccgtt tggctgttcg attgccctgg agccgctccg    10800
tgcagaaaat tgtgcagtgg gaagcatccc tatatctata gatatacccg atgcggcttt    10860
cactagaata tctgaaacac cgacagtctc agacctggaa tgcaaaatta cggagtgtac    10920
ttatgcctcc gatttcggtg gtatagccac cgttgcctac aaatccagta agcaggaaa    10980 ctgtccaatt cattctccat caggtgttgc agttattaaa gagaatgacg tcacccttgc    11040
tgagagcgga tcatttacat tccacttctc cactgcaaac atccatcctg cttttaagct    11100
gcaggtctgc accagtgcag ttacctgcaa aggagattgc aagccaccga agatcatat    11160 cgtcgattat ccagcacaac ataccgaatc ctttacgtcg gcgatatccg ccaccgcgtg    11220
gtcgtggcta aaagtgctgg taggaggaac atcagcattt attgttctgg ggcttattgc    11280
tacagcagtg gttgccctag ttctgttctt ccatagacat taacatcttg tcaaccacat    11340
aacactacag gcagtgtata aggctgtctt actaaacact aaattcaccc tagttcgatg    11400
tacttccgag ctatggtgac ggtggtgcat aatgccgccg atgcagtgca taaggctgct    11460
atattaccaa attataacac taagggcagt gcataatgct gctcctaagt aatttttatac   11520 acactttata atcaggcata attgccgtat atacaattac actacaggta atatactgcc    11580
tcttataaac actacaggca gcgcataatg ctgtcttta tatcaattta caaaatcata    11640
ttaatttttc ttttatgttt ttattttgtt tttaatattt caaaaaaaaa aaaaaaaaa    11700 aaagcggcgc cttcgaaggg cgaaattctg cagatattca tcacactggc ggccgctcga    11760
gcatgcatct agagg                                                     11775
```

<210> SEQ ID NO 2
<211> LENGTH: 5
<212> TYPE: PRT
<213> ORGANISM: Eastern equine encephalomyelitis virus

<400> SEQUENCE: 2

Arg Arg Thr Arg Arg
 1               5

<210> SEQ ID NO 3
<211> LENGTH: 5
<212> TYPE: PRT
<213> ORGANISM: Eastern equine encephalomyelitis virus

<400> SEQUENCE: 3

Cys Asn Ala Arg Arg
 1               5

<210> SEQ ID NO 4
<211> LENGTH: 5
<212> TYPE: PRT
<213> ORGANISM: Eastern equine encephalomyelitis virus

<400> SEQUENCE: 4

Cys Asn Ala Ser Arg
 1               5

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 5
tttccatgtg atcaacaccc tgttatgaaa agaatccaca cga                43

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 6
tcgtgtggat tcttttcata acagggtggt tgatcacatg gaaa               44

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 7
ccttaaaggc cttcaggatg aagctga                                  27

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 8
gggggggaag aggcttccga c                                        21

<210> SEQ ID NO 9
<211> LENGTH: 53
<212> TYPE: DNA
<213> ORGANISM: Artificial Sequence
<220> FEATURE:
<223> OTHER INFORMATION: Description of Artificial Sequence: Primer

<400> SEQUENCE: 9
gactgaattc agatctgtta atacgactca ctatagatag ggtacggtgt aga     53

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Primer -continued

<400> SEQUENCE: 10
gcctgctcct gcctcctgc                                                   19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
cgcaggtggt aaggacaggg                                                  20

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 12
cacttacacc cgatttaagt tcg                                              23

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 13
gtgatgccaa ttctgttcc                                                   19

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 14
taatatttca aaaaaaaaa aaaaaaaaa agcggccgc                                39

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 15
tgaaatgagt gtccaaatca gcattacatt tcacagc                                37

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 16
gctgtgaaat gtaatgctga tttggacact catttca                               37

<210> SEQ ID NO 17

```
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 17
gtcctgggtg gagtcaacg                                             19

<210> SEQ ID NO 18
<211> LENGTH: 30
<212> TYPE: DNA
<213> ORGANISM: Eastern equine encephalomyelitis virus
<220> FEATURE:
<221> NAME/KEY: CDS
<222> LOCATION: (1)..(30)

<400> SEQUENCE: 18 aat gct agg aga acc agg aga gat ttg gac                          30
Asn Ala Arg Arg Thr Arg Arg Asp Leu Asp
 1               5                  10

<210> SEQ ID NO 19
<211> LENGTH: 10
<212> TYPE: PRT
<213> ORGANISM: Eastern equine encephalomyelitis virus

<400> SEQUENCE: 19

Asn Ala Arg Arg Thr Arg Arg Asp Leu Asp
 1               5                  10
```

LIVE ATTENUATED VIRAL VACCINES FOR EASTERN EQUINE ENCEPHALITIS VIRUS

The present application claims priority under 35 U.S.C. §119 of U.S. provisional application No. 60/474,752, filed May 29, 2003, incorporated herein in its entirety by reference.

GOVERNMENT INTEREST

The invention described herein may be manufactured, used and licensed by or for the U.S. Government.

BACKGROUND OF THE INVENTION

1. Field of the Invention

The present invention relates to a vaccine against Eastern Equine Encephalitis (EEE) virus. More specifically the invention relates to the synthesis of an alphavirus, EEE clone that is useful as a vaccine for EEE. cDNAs coding for an infectious Eastern equine encephalitis virus are disclosed. Novel attenuating mutations and their use are described.

2. Brief Description of Related Art

Eastern equine encephalitis (EEE), Western equine encephalitis (WEE), and Venezuelan equine encephalitis virus (VEE) are members of the *Alphavirus* genus of the family *Togaviridae*. The genus is comprised of at least 27 different arthropod-borne RNA viruses that are found throughout much of the world. The viruses normally circulate among avian or rodent hosts through the feeding activities of a variety of mosquitoes. Many epizootics have occurred and they correlate with increased mosquito activity after periods of increased rainfall.

Based on comparisons of their genomic sequences, EEE, WEE and VEE appear to be closely related New World alphaviruses. All three viruses are known to cause encephalitis in humans and equines in epidemic proportions. However, EEE causes the most severe of the arboviral encephalitides in humans, with 50-75% mortality and severe neurological sequelae in survivors (Fields Virology, 4$^{th}$ Ed., Chapter 30 Alphaviruses, [2002] 917-962). The highest case fatality rates occur in children and the elderly. In equines, the mortality rate is substantially higher, ranging from 80-90% with most survivors having significant neurologic sequela (Weaver et al. [1989] Adv Virus Res. 37:277-328). EEE outbreaks have also been observed in pigs (Elvinger et al. [1996] J Vet Diagn Invest 8:481-484) as well as in game birds such as pheasants (Sussman et al. [1958] Ann NY Acad Sci 70:328-341) and emus (Tully et al. [1992] Avian Dis 36:808-812).

In EEE epidemics, *Aedes* and *Coquillettidia* mosquito species are thought to bridge the gap between infected birds and humans or equines. The recent advances of the *Aedes albopictus* mosquito in North America and its known competence as an EEE vector has increased the potential for more frequent and widespread epidemics and enzootics (Mitchell et al., [1992] Science 257: 526-527). Another significant public health concern involves infected migratory birds carrying the virus into new areas. Studies have shown that this occurs. Two South American strains of EEE virus were isolated from migratory birds captured in Mississippi in the early 1970's (Calisher et al. [1971] Am J Epidemiol 94:172-178). In 1996 an EEE equine epidemic occurred in Tamaulipas State, Mexico. This area is several hundred miles outside of the geographic range of the natural EEE vector and epidemiologists believe it was caused by infected migratory birds (Brault et al. [1999] Am J Trop Med Hyg. 61:579-586).

EEE was first recognized as an equine disease in the northeastern U.S. The virus responsible for EEE was originally isolated from the brains of infected horses involved in a 1933 outbreak in Virginia and New Jersey (Ten Broeck, C. et al. [1933] *Proc. Soc. Exp. Biol. Med.* 31:217-220.). EEE virus has caused localized outbreaks in equines, pigs, pheasants, emus and humans during the summer months in North America. The virus is known to be focally endemic along much of the Atlantic and Gulf Coasts of North America. It has also been found in southern Canada, the Caribbean, Central America, the eastern part of Mexico and in large sections of South America. (FIG. 2). Inland foci exist in the Great Lakes region and South Dakota in the U.S. as well as the Amazon Basin.

The current EEE vaccine for human use and veterinary applications in the U.S. is a formalin-inactivated whole virus preparation derived from the PE-6 strain (Bartelloni, et al. [1970] Am J. Trop Med Hyg. 19:123-126; Marie, et al. [1970] Am J Trop Med Hyg. 19:119-122). This preparation is currently licensed for veterinary use. For humans it is an investigative new drug (IND) and is intended for persons at risk for infection (e.g., laboratory and field investigative personnel). This inactivated vaccine is poorly immunogenic, requires multiple inoculations with frequent boosters and generally results in immunity of short duration (Pittman et al. in Vaccines, 4$^{th}$ Ed. (Eds. Plotkin, S. A. and Orenstein, W. A.) [2004] pgs. 991-992). Another important shortcoming is that this inactive EEE vaccine provides inadequate protection against antigenically distinct South American EEE strains [Strizki et al. [1995] Am J Trop Med Hyg. 53:564-570; Dietz et al. [1980] Am J Trop Med Hyg. 29:133-140]. Last, there are dire consequences if the PE-6 vaccine preparation is not fully inactivated. Recently, an improperly inactivated PE6 preparation is suspected of causing fatal EEE encephalitis in a California equine (Franklin et al. [2002] Emerging Infectious Diseases 8:283-288).

The scientific community considers EEE to be a virus that could potentially be used as a biological weapon. The Centers for Disease Control (CDC) has categorized EEE as a class B select agent. Scientists within the ex-Soviet Union have conducted "vaccine" research on the virus (Volchkov et al. [1991] Molekulyarnaya Genetika 5: 8-15) despite the fact that the virus is only endemic to the Western Hemisphere.

The shortcomings of the only available EEE vaccine indicate a need for the development of a new formulation. A live attenuated vaccine could offer significant advantages for both human and veterinary use over the inactivated PE-6 preparation. These benefits include administration being limited to a single dose and more efficient production of humoral immunity. A live, attenuated vaccine could also be produced from less starting material than is possible with existing inactivated products. Last, it may provide immunity to EEE that can last for several years or even for life and protect against all strains of EEE.

Deletion of the furin protease cleavage site from VEE and WEE viruses has resulted in the successful production of live-attenuated vaccine candidates. Each of these approaches has been previously patented by others (U.S. Pat. Nos. 6,261, 570 and 5,505,947). Research on EEE virus has lagged significantly behind VEE and WEE despite it being the most dangerous of these viruses. To date, there is no known viable EEE vaccine that contains a full or partial deletion of the furin cleavage site.

Therefore, it is an object of the present invention to produce a live attenuated EEE vaccine composed of a furin-cleavage deletion mutant. This vaccine will be derived from a molecular clone of EEE constructed from cDNAs encompassing the entire genome of EEE. This construct will contain a full or partial deletion of the furin cleavage site and/or other deletions within the EEE genome.

The classical method of deriving live-attenuated vaccines involves blind passage of virus in cell cultures. This approach was used successfully to produce alphavirus vaccines for VEE (TC83) and chikungunya (Vaccines, 4$^{th}$ Ed., Chapter 35 Miscellaneous limited-use vaccines, [2004] 991-992). A dis-advantage of this approach is that it often results in heterogonous products. We have utilized this classical method in the development of several EEE vaccine candidates. To address any ambiguities attenuated viruses were always sequenced and we subsequently produced defined, molecular clones that behaved comparably to the parental virus.

The alphavirus genome is a single-stranded, positive sense RNA approximately 11,700 nucleotides in length. The 5' two-thirds of the genome consist of a non-coding region of approximately 46 nucleotides followed by a single open reading frame of approximately 7,500 nucleotides which encodes the viral replicase/transcriptase. The 3' one-third of the genome encodes the viral structural proteins in the order Capsid-E3-E2-6K-E1, each of which are derived by proteolytic cleavage of the product of a single open reading frame of approximately 3,700 nucleotides. The sequences encoding the structural proteins are transcribed as a 26S mRNA from an internal promoter on the negative sense complement of the viral genome. The nucleocapsid (C) protein possesses autoproteotytic activity which cleaves the C protein from the precursor protein soon after the ribosome transits the junction between the C and E3 protein coding sequence. Subsequently, the envelope glycoproteins E2 and E1 are derived by proteolytic cleavage in association with intracellular membranes and form heterodimers. E2 initially appears in the infected cell as the precursor protein PE2, which consists of E3 and E2. After extensive glycosylation and transit through the endoplasmic reticulum and the golgi apparatus, E3 is cleaved from E2 by the furin protease at a cleavage site having a consensus sequence of RXK/RR, with X being one of many amino acids present in the different viruses and cleavage occurring after the last arginine (R) residue. Subsequently, the E2/E1 complex is transported to the cell surface where it is incorporated into virus budding from the plasma membrane (Strauss and Strauss [1994] Microbiological Rev. 58: 491-562). All documents cited herein supra and infra are hereby incorporated in their entirety by reference thereto. A diagram of the EEE virus genome is shown in FIGS. 3 and 4.

Because the genome of alphaviruses are positive-stranded RNA, and infectious upon transfection of cells in culture, an "infectious clone" approach to vaccine development is particularly suitable. In this approach, a full-length cDNA clone of the viral genome is constructed downstream from a RNA polymerase promoter, such that RNA which is equivalent to the viral genome can be transcribed from the DNA clone in vitro. This permits one to conduct site-directed mutagenesis to insert specific mutations into the DNA clone, which are then reflected in the virus which is recovered by transfection of the RNA.

Previous work with infectious clones of other alphaviruses has demonstrated that disruption of the furin cleavage site results in a virus which incorporates Precursor E2 Protein (PE2) into the mature virus. Davis et al. (1995 supra) found that disruption of the furin cleavage site in an infectious clone of VEE is a lethal mutation. Transfection of BHK cells with RNA transcribed from this mutant clone resulted in the release of non-infectious particles. However, a low level of infectious virus was produced which contained secondary suppressor mutations such that PE2-bearing virus was fully replication competent. It was subsequently shown to be avirulent but capable of eliciting immunity to lethal virus challenge in a variety of animal species.

The genetic basis for attenuation of the VEE TC-83 vaccine and certain laboratory strains of VEE virus (e.g. V3526) have been studied extensively and has led to the development of improved live, attenuated vaccine candidates (Davis et al. 1995, surpa; Pratt et al., [2003] Vaccine 21:3854-3862). The approach used in this application is similar to that used for VEE, however, following the VEE example did not result in an adequate vaccine for EEE. Changes in the procedure used for VEE were required in order to produce the attenuated live EEE virus of the present invention. None of which could have been predicted from previous alphavirus research.

Based upon a comparison of the structural protein gene sequences of EEE and other alphaviruses, the probable furin cleavage site of EEE strain FL91-4697 virus is RRTRR (SEQ ID NO: 2). The presence of the extra arginine when compared to the furin consensus sequence (RX(R/K)R) indicates that cleavage at this site might be more complex than that observed for VEE virus. It was necessary, therefore, to prepare a deletion mutant in the E3-E2 cleavage site of the full-length clone which lacked five amino acids to produce an attenuated virus. The residual arginine in the full-length clone was of concern due to the possibility that other mutations might arise due to the presence of the extra arginine resulting in cleavage by cellular proteases at that site and producing an apparently wild type (wt) virus with respect to cleavage of PE2.

Transfection of cultured cells with RNA transcribed from an infectious clone of EEE lacking either a partial or full deletion of the furin cleavage site yielded viruses which contained the PE2 of EEE in the mature virus but which were not replication competent. During intracellular replication of the RNA, mutations arise at low frequency, resulting in a small number of replication competent viruses. Sequence analysis of these viruses has shown that the lethal effect of the deletion mutations was alleviated by the appearance of second site mutations in the E3, E2 and/or E1 glycoproteins. These viruses are attenuated in mice when administered by subcutaneous or intranasal inoculation. The inoculated mice produced a high titer of serum neutralizing antibody specific to EEE and were protected against a lethal, aerosol challenge of parental virulent EEE virus (>1000×LD50). Similar results were observed in young chickens when mutant EEE viruses were administered by subcutaneous inoculation. The birds produced neutralizing antibody and were protected against a subcutaneous (s.c.) challenge of the parental FL91 EEE virus as well as the South American PE-0155 strain of EEE.

Therefore, in one aspect of the invention, the invention pertains to the isolation of a cDNA sequence coding for wild type infectious eastern equine encephalitis (EEE) virus RNA transcript. DNA representing the entire FL91-4679 genome, not previously available, was prepared by polymerase chain reaction using a series of primer pairs based upon the genome sequence of the PE-6 stain of EEE. In order to determine the correct sequence at the 5' and 3' ends of the genome, a protocol called rapid amplification of cDNA ends (RACE) was used. The full length clone is useful in the production of virulent EEE virus and as a platform to introduce and test attenuating mutations. The production of virulent virus is essential for a formal measure of the degree of attenuation achieved with candidate attenuating mutations and a formal determination of the rate at which reversion to virulence might occur.

Portions of the EEE cDNA sequences described above are also useful as probes to diagnose the presence of virus in samples, and to define naturally occurring variants of the virus. These cDNAs also make available polypeptide sequences of EEE antigens encoded within the EEE genome, and permit the production of polypeptides which are useful as standards or reagents in diagnostic tests and/or as components of vaccines. Antibodies, both polyclonal and monoclonal, directed against EEE epitopes contained within this polypeptide sequence would also be useful for diagnostic tests, as therapeutic agents, and for screening of antiviral agents.

Accordingly, with respect to polynucleotides, some aspects of the invention are: a purified EEE polynucleotide, a recombinant EEE polynucleotide to include chimeric viruses; a recombinant polynucleotide comprising a sequence derived from an EEE genome or from EEE cDNA to include a chimeric virus; a recombinant polynucleotide encoding an epitope of EEE, a recombinant vector containing any of the above recombinant polynucleotides, and a host cell transfected with any of these vectors.

Another aspect of the invention is a single-stranded DNA sequence comprising a cDNA clone coding for an infectious EEE, the cDNA clone including at least one attenuating mutation therein, the RNA produced from transcription of the cDNA and the virus particles produced from the RNA in a host cell for use as a vaccine.

In another aspect of the invention there is provided a full length EEE cDNA clone containing a defined deletion mutation useful for attenuating the virus for the identification of suppressor mutations in the virus. The attenuated viruses with the cleavage deletion and suppressor mutations are useful as a means to generate an attenuated, live EEE virus vaccine for veterinary and human use.

In a further aspect of the invention is provided a chimeric virus containing nonstructural and/or structural protein gene sequences derived from EEE and protein gene sequences from any alphaviruses including but no limited to Aura, Barmah Forest, Bebaru, Cabassou, Chikungunya, Everglades, Fort Morgan, Getah, Highlands J, Kyzylagach, Mayaro, Middelburg, Mucambo, Ndumu, O'nyong-nyong, Pixuna, Ross River, Sagiyama, Semliki Forest, SAAR87, Sindbis, Tonate, Una, Venezuelan equine encephalitis, Western equine encephalitis and Whataroa, which could be used as a means for attenuating virulent alphaviruses. Depending on the non-EEE sequences substituted for EEE, another aspect of the invention includes a means to express antigens of other alphaviruses as chimeric alphaviruses as potential vaccines for human and veterinary use.

In a further aspect of the invention, there is provided a vaccine protective against EEE, the vaccine comprising live attenuated EEE virus in an amount effective to elicit protective antibodies in an animal to EEE and a pharmaceutically acceptable diluent, carrier, or excipient.

In yet another aspect of the invention there is provided an inactivated vaccine produced from the live attenuated virus described above. The attenuated virus of the present invention whether whole virus or chimeric virus, can be used in producing inactivated virus vaccines. By using an attenuated EEE virus strain, there is a much greater margin of safety in the event that the product is incompletely inactivated. Starting with an attenuated strain is also much safer during the manufacturing phase, and allows production under lower biocontainment levels.

The live-attenuated EEE vaccine candidates disclosed hereafter are primarily predicated upon deletion of the furin-cleavage site. The present invention has evolved through a 3-tier approach to produce the candidates disclosed and claimed herein.

These and other objects will become apparent upon further reading of this disclosure. In this application are described live attenuated vaccines for EEE which may provide higher level immunity in humans.

SUMMARY OF THE INVENTION

The present invention satisfies the need mentioned above. In this application are described live attenuated vaccines for EEE which may provide higher level immunity in humans and equines for many years, and possibly for life. In addition, very large numbers of vaccine doses can be produced from significantly less starting materials than is possible with the existing inactivated products. The vaccine preparations of the present invention comprise full-length cDNA copies of the EEE genome which has been altered such that the RNA produced from the cDNA, and the virus produced there from is attenuated and useful as a live vaccine for human and veterinary use. The vaccine preparations for EEE are novel viruses which include deletions in the structural protein coding region.

BRIEF DESCRIPTION OF THE DRAWINGS

FIG. 1A. The assembly of the full length cDNA clone of eastern equine encephalitis virus. Polymerase chain reaction products representing the entire genome of EEE virus were prepared with the primer pairs indicated. Each of the products was cloned into pBluescript KS+. Assembly of the full length clone, pEE2002 in pBluescript was carried out as indicated in the figure and described below. The clones are not drawn to scale. In each of the plasmids, the primers used to generate the PCR products are indicated as are the restriction endonuclease sites used for the assembly. The oligonucleotides are shown in SEQ ID NOS 7-17, respectively, in order of appearance.

FIG. 3 is a diagram of the organization and expression of EEE virus genome (RRTRR peptide shown in SEQ ID NO: 2);

FIG. 5 is a flow diagram of the strategy for the construction of a genetically engineered EEE vaccine;

FIG. 6 is a diagram of Example 2 EEE mutations;

FIG. 8 is a diagram of furin cleavage in EEE envelope glycoprotein processing (see SEQ ID NOS 18-19);

FIG. 9 is a chart showing serial passage of pEE4202 mutant EEE;

Figure 10:
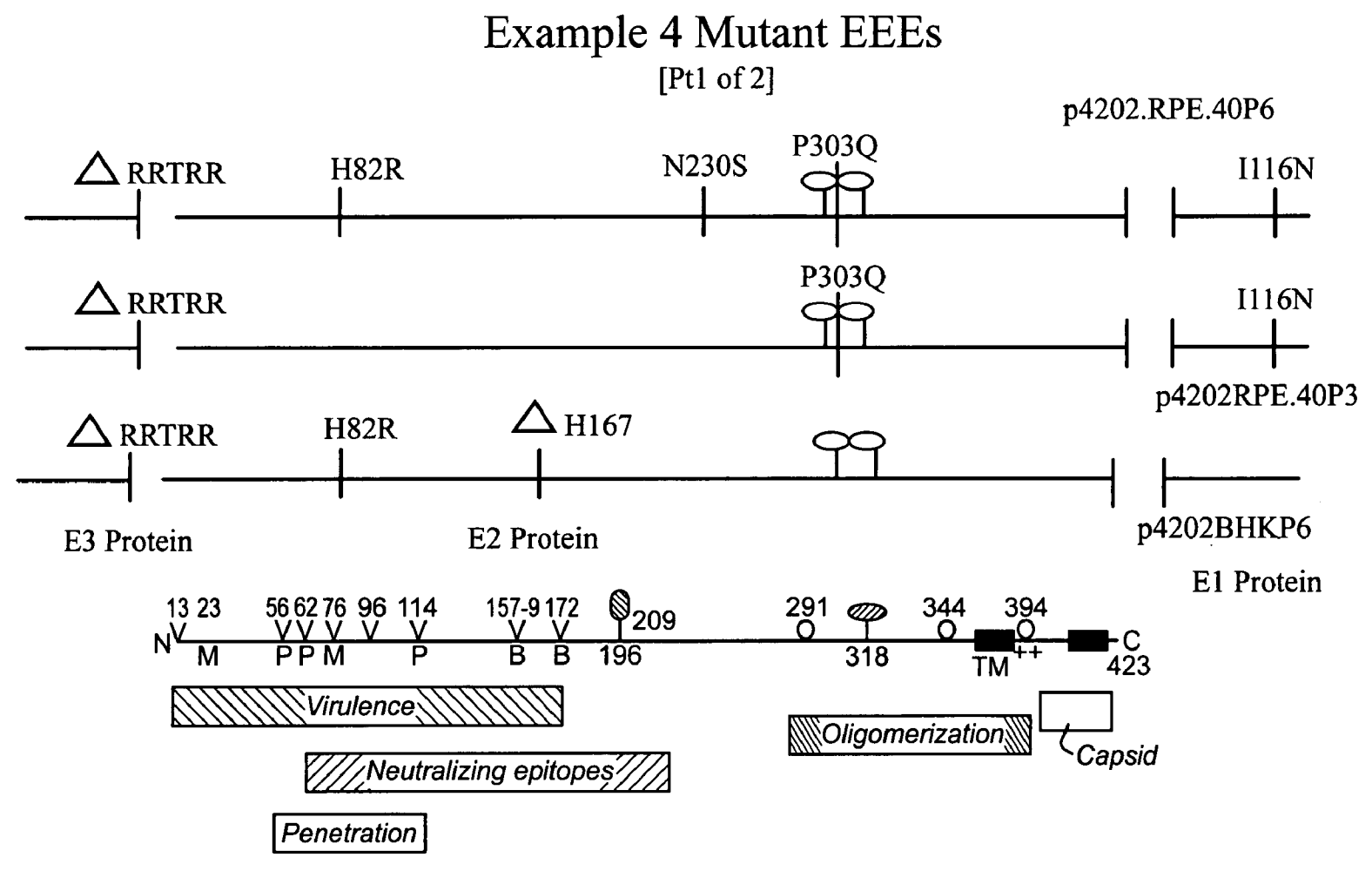

FIG. 10 is a diagram of Example 4 mutant EEEs (RRTRR peptide shown in SEQ ID NO: 2);

Figure 11:
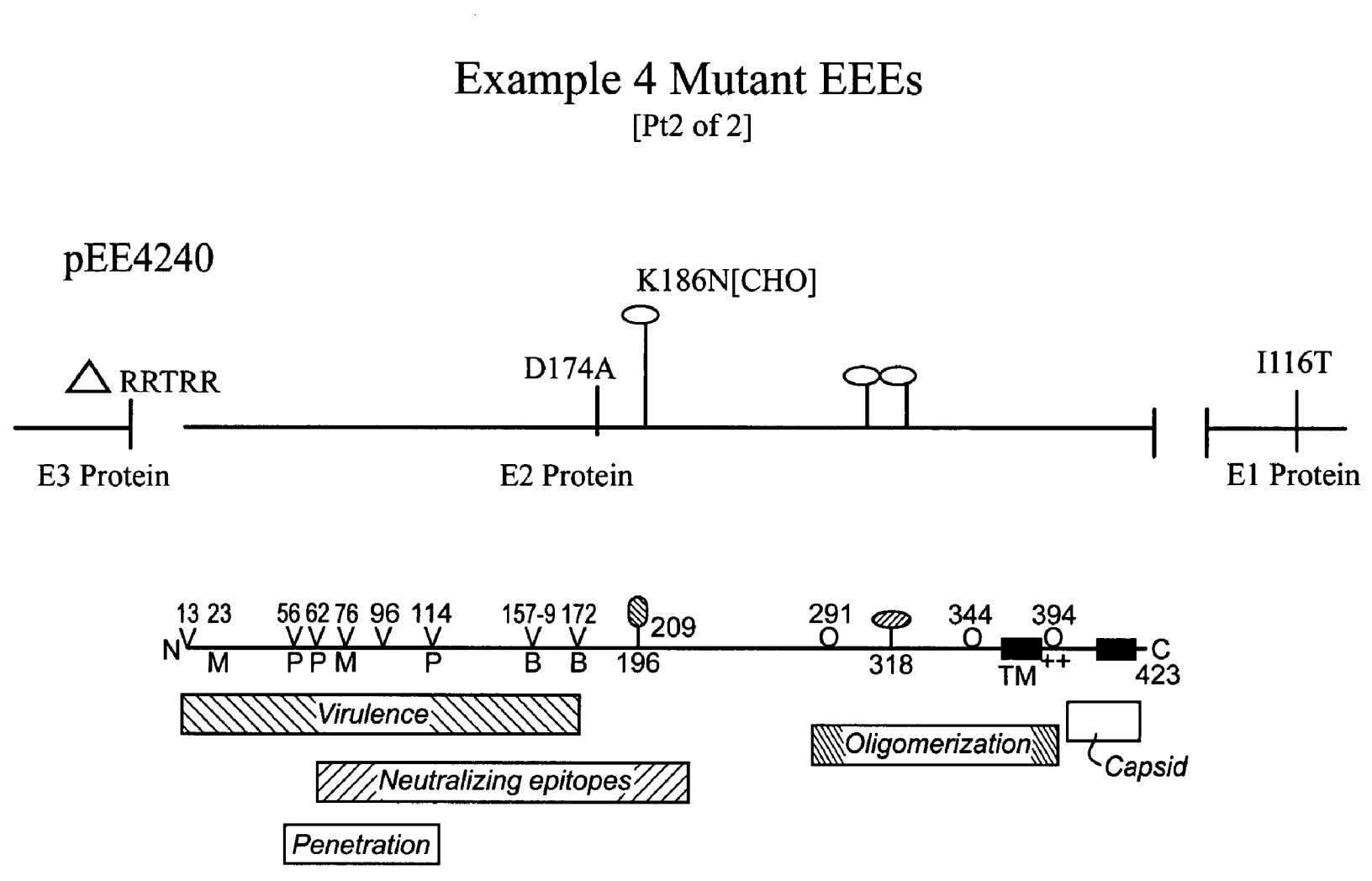

FIG. 11 is a diagram of Example 4 mutant EEEs (RRTRR peptide shown in SEQ ID NO: 2);

DETAILED DESCRIPTION

Figure 1B:
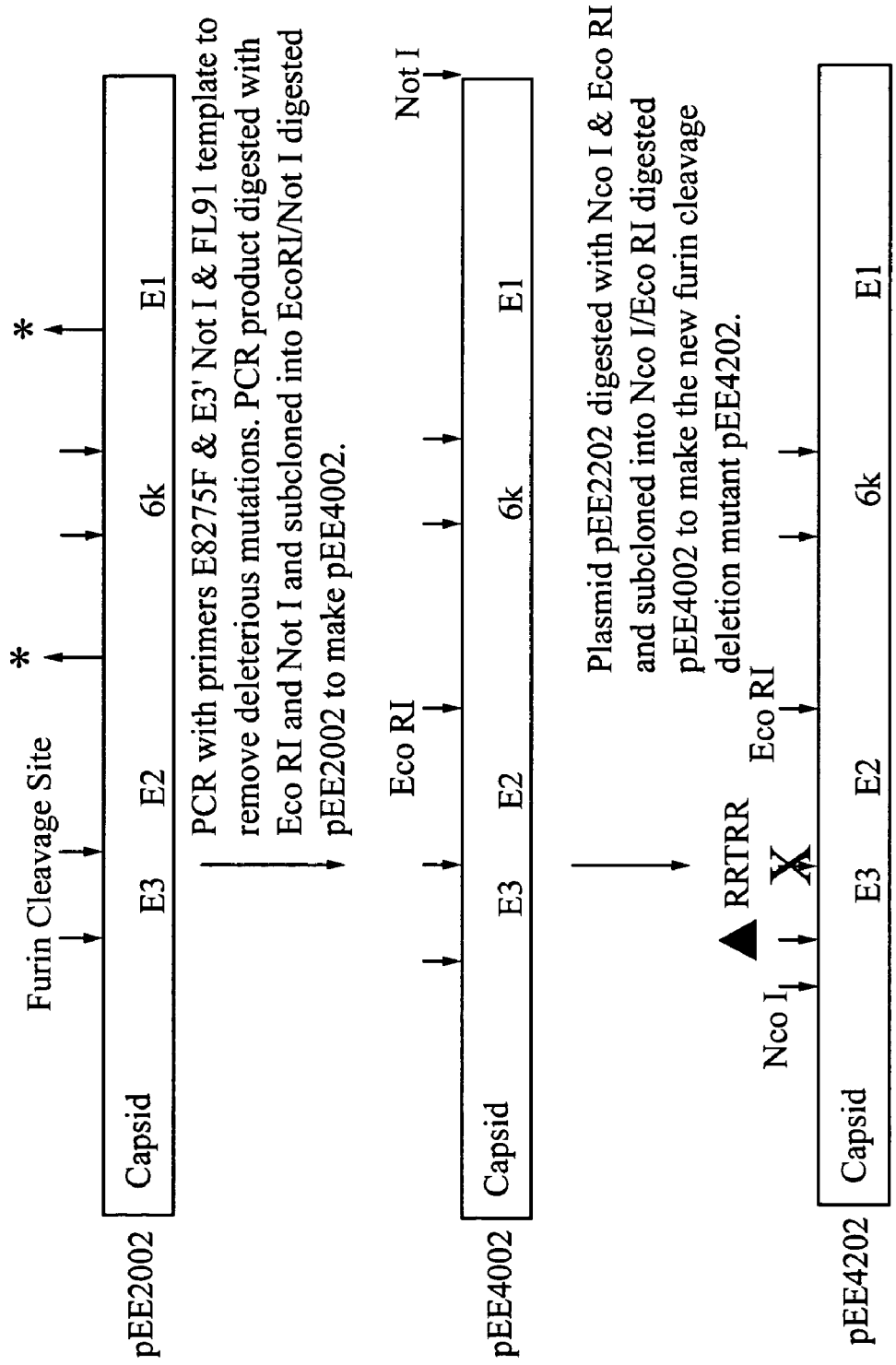
FIG. 1B. Derivation of the second generation full length cDNA clones for eastern equine encephalitis virus. A PCR product was generated using the wt FL91 cDNA and primers E8275F and E3'Not I. This PCR product was digested with Eco RI and Not I and the resulting DNA fragment was subcloned into pEE2002. This resulted in the production of a new infectious plasmid, pEE4002. The deleterious cystiene point mutations (*) were absent from the final full-length clone pEE4002. An Nco I/Eco RI fragment from pEE2202 was subcloned into pEE4002 to make the new furin cleavage deletion mutant pEE4202. The RRTRR peptide shown in SEQ ID NO: 2
Figure 1C:
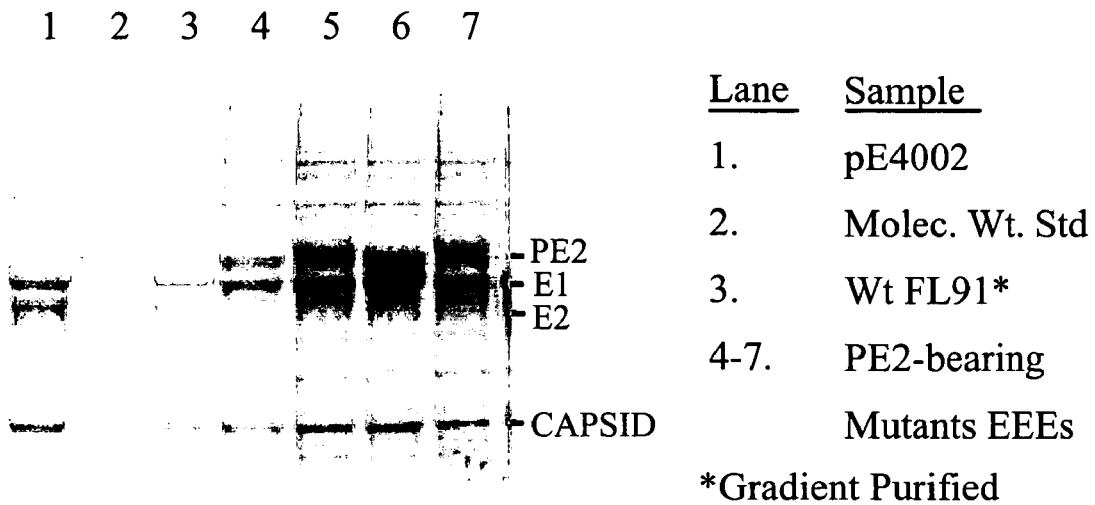
FIG. 1C. Polypeptide profiles of eastern equine encephalitis viruses. Samples of purified virus were analyzed by electrophoresis on 10% polyacrylamide gels and stained with Coomassie Brilliant blue. Lane 1 contains recombinant virus pEE4002 (i.e. the wtFL91 molecular clone), Lane 2 contains a molecular weight marker (molecular weights from top to bottom are 200.0, 116.3, 97.4, 66.3, 55.4, 36.5, 31.0, 21.5 and 14.4 kilodaltons), Lane 3 represents the uncloned wt FL91-4679 virus and Lanes 4-7 contain pEE4202 furin protease cleavage deletion viral mutants that contain PE2 protein and lack E2.
Figure 2:
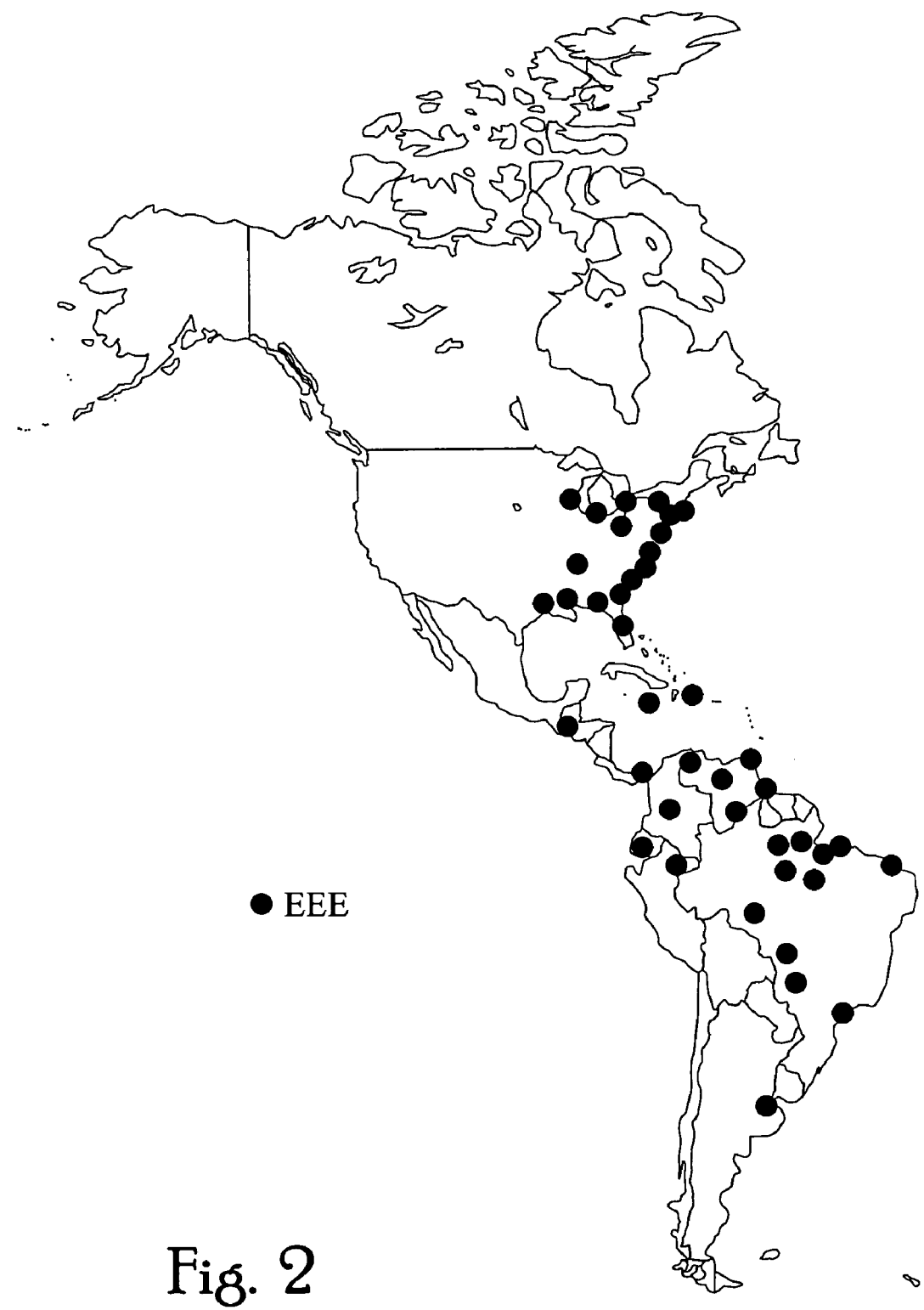
FIG. 2 is a map showing the geography of the presence of EEE.
Figure 4:
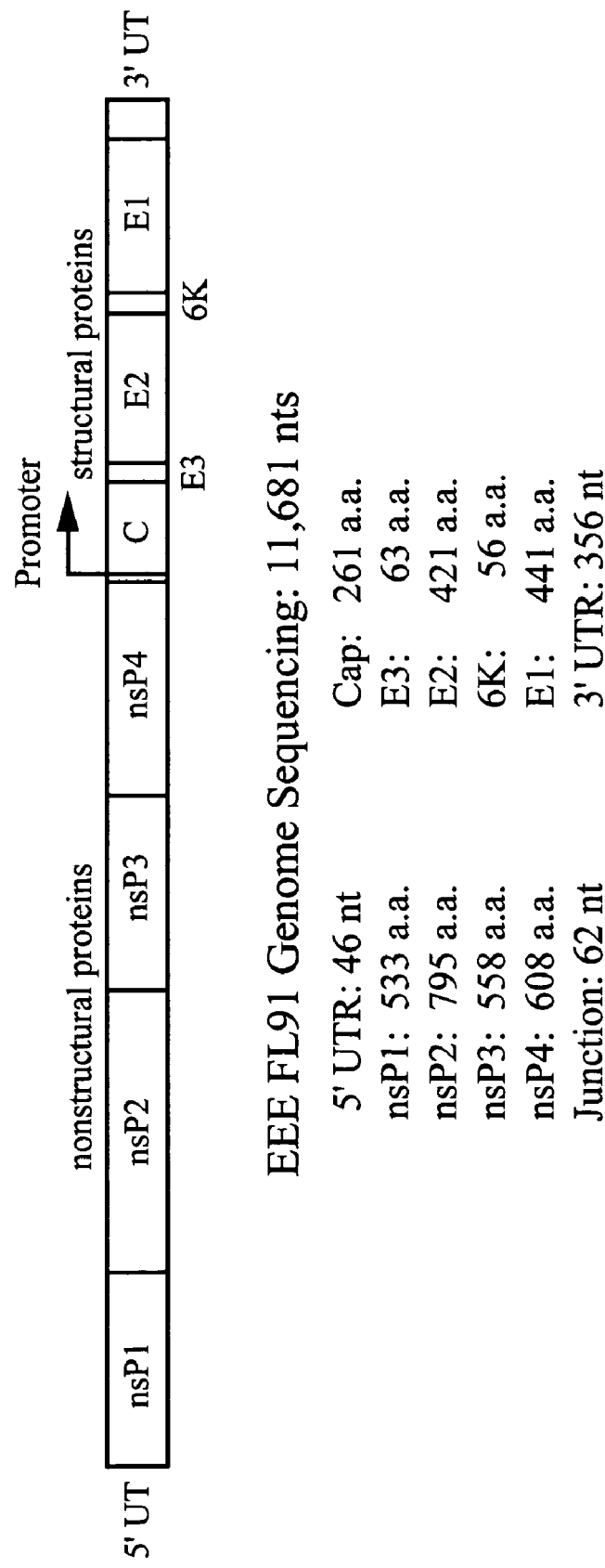
FIG. 4 is a diagram of the EEE FL91 Genome.
Figure 7:
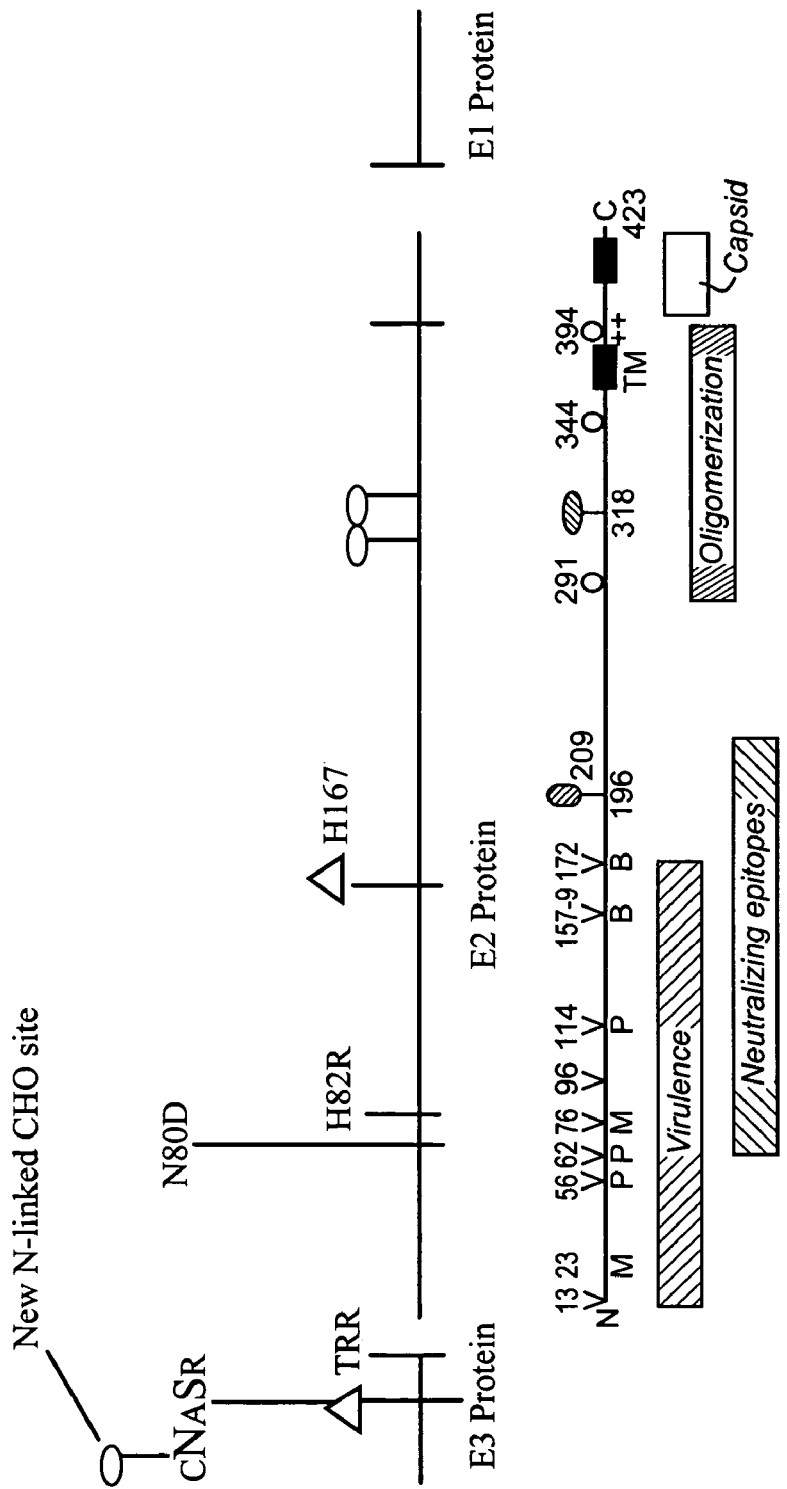
FIG. 7 is a diagram of Example 3 EEE mutations.

In one embodiment, the present invention relates to a full length cDNA clone of fully virulent EEE virus (pEE 4002) specified in SEQ ID NO: 1

EEE, strain FL91-4679, was isolated from infected *Aedes albopictus* mosquitoes isolated in 1991 from Polk County, Florida (Mitchell et al., [1992] Science 257 (5069): 526-527.). This virus was used as a parent strain in the instant invention. Any isolate known to cause disease in man or animals can be chosen. Preferably a strain which consistently kills 100% of young mice when inoculated subcutaneously can be used. In addition the ability of a strain to have an easily identifiable phenotype such as, for example, the ability to form large plaques in tissue culture on indicator cell monolayers, is helpful.

The cDNA clone can be generated by any of a variety of standard methods known in the art. Preferably, DNA representing the entire genome can be prepared by polymerase chain reaction (PCR) using a series of primer pairs based upon any of the North American EEE genome sequences previously deposited in GenBank. The 5' terminal sequence of the virus may be determined by 5'-RACE basically as described by Frohman et al. ([1988] Proc. Natl. Acad. Sci. U.S.A. 85:8998-9002). Assembly of the full length clone can be in a suitable transcription vector such as, for example, pBluescript KS+, using convenient restriction endonuclease sites or the entire genome could be inserted into any plasmid which contains suitable restriction endonuclease cleavage sites for cloning, an origin of replication so that the plasmid can be propagated in a bacterial host, and a selectable marker gene to maintain the plasmid in the bacterial cell during growth. The DNA sequence preferably has a complementary DNA sequence bonded thereto so that the double-stranded sequence will serve as an active template for RNA polymerase. Hence, the transcription vector preferably comprises a plasmid. When the DNA sequence comprises a plasmid, it is preferred that a unique restriction site be provided 3' (with respect to the virion RNA sequence) to ("down-stream" from) the cDNA clone. This provides a means for linearizing the DNA sequence to enhance the efficiency of transcription of genome-length RNA in vitro.

The complete clone is preferably operatively associated with a promoter region such that the promoter causes the cDNA clone to be transcribed in the presence of an RNA polymerase which binds to the promoter. The promoter is positioned on the 5' end (with respect to the virion RNA sequence), or upstream from, the cDNA clone. An excessive number of nucleotides between the promoter sequence and the cDNA clone will result in the inoperability of the construct. Hence, the number of nucleotides between the promoter sequence and the cDNA clone is preferably not more than eight, more preferably not more than 5, still more preferably not more than 3, and most preferably not more than 1.

Exemplary promoters useful in the present invention include, but are not limited to, T3 promoters, T7 promoters, and SP6 promoters. It is preferable that the 5' end of the in vitro transcript not have any additional nucleotides preceding the first nucleotide of the viral sequence. At the 3' end, additional nucleotides can be tolerated in the in vitro transcript but are probably lost when the virus replicates. In most instances, the poly-A tract at the 3' end is required for viability of the virus. Selection of the virulent full length clone can be achieved by comparing the LD.sub.50 of the virus encoded by the cloned cDNA with the LD.sub.50 of the parent virus used, in the instant example, EEE FL91-4679.

The ability to produce virulent virus is important; it allows the introduction and testing of attenuation mutations and the attenuated phenotype against a standard: the virulent parent.

Transfection of cells with the RNA transcript coded by the full length genomic cDNA can be achieved by any suitable means, such as, for example, by treating the cells with DEAE dextran, treating the cells with liposomes, and by electroporation. Togavirus-permissive cells, alphavirus-permissive cells, and EEE-permissive cells are cells which, upon transfection with the viral RNA transcript, are capable of producing viral particles. Togaviruses have a broad host range. Examples of such cells include, but are not limited to, Vero cells, baby hamster kidney cells, chicken embryo fibroblast cells, Chinese hamster ovary cells (CHO), African green monkey kidney cells (COS-7), mouse L cells, MRC-5 cells, mosquito cells such as C6-36 cells, to name a few.

To determine virulence of the cloned viral genome, mice can be inoculated intranasally or subcutaneously with 10.sup.5 plaque forming units (pfu) of the cloned virus. The clone is considered virulent if all mice die, and not fully virulent if all mice do not die. The LD.sub.50 of parent EEE strain FL91-4679 via aerosol is approximately 50 pfu. Therefore, if inoculation of 1,000-fold did not cause lethal disease in all mice, it was considered attenuated.

DNA or polynucleotide sequences to which the invention also relates include sequences of at least about 6 nucleotides, preferably at least about 8 nucleotides, more preferably at least about 10-12 nucleotides, most preferably at least about 15-20 nucleotides corresponding, i.e., homologous to or complementary to, a region of the EEE nucleotide sequence. Preferably, the sequence of the region from which the polynucleotide is derived is homologous to or complementary to a sequence which is unique to the virus. Whether or not a sequence is unique to the virus can be determined by techniques known to those of skill in the art. For example, the sequence can be compared to sequences in databanks, e.g., GenBank. Regions from which typical DNA sequences may be derived include but are not limited to, for example, regions encoding specific epitopes, as well as non-translated regions.

The derived polynucleotide is not necessarily physically derived from the nucleotide sequence of the alphaviruses, but may be generated in any manner, including for example, chemical synthesis or DNA replication or reverse transcription or transcription, which are based on the information provided by the sequence of bases in the region(s) from which the polynucleotide is derived. In addition, combinations of regions corresponding to that of the designated sequence may be modified in ways known in the art to be consistent with an intended use. The sequences of the present invention can be used in diagnostic assays such as hybridization assays and polymerase chain reaction assays and for the discovery of other alphavirus sequences.

A polypeptide or amino acid sequence derived from the amino acid sequence of alphavirus, refers to a polypeptide having an amino acid sequence identical to that of a polypeptide encoded in the sequence, or a portion thereof wherein the portion consists of at least 2-5 amino acids, and more preferably at least 8-10 amino acids, and even more preferably at least 11-15 amino acids, or which is immunologically identifiable with as a polypeptide encoded in the sequence.

A recombinant or derived polypeptide is not necessarily translated from a designated nucleic acid sequence, it may be generated in any manner, including for example, chemical synthesis, or expression of a recombinant expression system. Once a complete viral genomic cDNA is cloned, attenuation of the virus is possible. An attenuating mutation refers to a nucleotide mutation or amino acid coded for in view of such a mutation which results in a decreased probability of causing disease in its host (i.e., a loss of virulence), in accordance with standard terminology in the art. The attenuating mutation may be a substitution mutation or an in-frame deletion mutation.

Novel attenuating mutations can be discovered in the EEE genome by introducing mutations which are not reparable by the viral RNA replication process. A preferable mutation is the deletion of the five amino acid furin protease cleavage site between the E3 and E2 proteins. Transfection of the mutant viral genome into cells can result in the suppression of the lethal effect of the deletion mutation due to the error prone process of alphavirus replication. Once efficiently replicating viral progeny is generated they can be detected by plaque assays and analyzed for the presence of PE2 protein which indicates that the virus contains the deletion mutation.

Attenuated but yet immunogenic virus with a cleavage deletion mutation and suppressor mutations could be tested for its ability to protect animals from challenge with virulent EEE.

Attenuating mutations may be introduced into cDNAs encoding live EEE by any suitable means, such as site-directed mutagenesis (Please see e.g., Maniatis, Fritsch and Sambrook, Molecular Cloning: A Laboratory Manual (1982) or DNA Cloning, Volumes I and II (D. N. Glover ed. 1985) or Current Protocols in Molecular Biology, Ausubel, F. M et al. (Eds.) John Wiley & Sons, Inc., for general cloning methods.).

In another embodiment, the attenuated viruses of the present invention can be used to prepare replicon expression systems. A replicon expression system consists of three components (Pushko et al. [1997] Virology 239: 389-401). The first is a replicon which is equivalent to a full length infectious clone from which all of the viral structural proteins have been deleted. A multiple cloning site can be cloned into the site previously occupied by the structural protein genes. Virtually any heterologous gene may be cloned into this cloning site. Transcription of RNA from the replicon yields RNA capable of initiating infection of the cells identically to that seen with the full-length infectious virus clone. However, in lieu of the viral structural proteins, the heterologous antigen is expressed. This system does not yield any progeny virus particles because there are no viral structural proteins available to package the RNA into particles.

Particles which appear structurally identical to virus particles can be produced by supplying structural proteins for packaging of the replicon RNA in trans. This is typically done with two helpers. One helper consists of a full length infectious clone from which the nonstructural protein genes and the glycoprotein genes are deleted. The helper retains only the terminal nucleotide sequences, the promoter for subgenomic mRNA transcription and the sequence for the viral nucleocapsid protein. The second helper is identical to the first except that the nucleocapsid gene is deleted and only the glycoprotein genes are retained. The helper RNA's are transcribed in vitro and co-transfected with replicon RNA. Because the replicon RNA retains the sequences for packaging by the nucleocapsid protein, and because the helpers lack these sequences, only the replicon RNA is packaged by the viral structural proteins and released from the cell. The particles can then be inoculated into animals similar to parent virus. The replicon particles will initiate only a single round of replication because the helpers are absent, they produced no progeny virus particles, and express only the viral non-structural proteins and the product of the heterologous gene cloned in place of the structural proteins. The heterologous gene product is then detected by the host immune system and appropriate immune response is then mounted.

The EEE replicon can be used to express heterologous genes of interest as well as a means for expressing antigens or immunogenic proteins and peptides of interest, in vitro or in vivo. The immunogenic protein or peptide, or "immunogen" may be any immunogen suitable for inducing an immune response protective against a pathogen from which the immunogen is derived, including but not limited to microbial, bacterial, protozoan, parasitic, and viral pathogens. For example, the immunogen can be the expression product of any heterologous gene of interest, including influenza hemagglutinin, Lassa fever nucleocapsid and glycoproteins, portions of bacterial toxin genes, HIV glycoprotein, Ebola glycoprotein, to name a few.

In yet another embodiment, the present invention provides inactivated virus vaccines produced from live attenuated virus preparations, either as virus with attenuating mutations as has been described or as chimeric viruses. The inactivation of live virus is well known in the art and can be performed, for example, by the use of formalin. Inactivated attenuated virus vaccine has a greater safety margin both as a final vaccine in case of incomplete inactivation and during the manufacturing process allowing production under lower biocontainment levels.

Subjects that may be administered the live attenuated or inactivated attenuated viruses and vaccine formulations disclosed herein include humans, mammals and birds (e.g. horse, donkey, pig, mice, hamster, monkey, birds, etc.).

Vaccine formulations of the present invention comprise an immunogenic amount of a live attenuated virus, or a combination of live attenuated viruses as a multivalent vaccine, as disclosed herein combination with a pharmaceutically acceptable carrier. An "immunogenic amount" is an amount of the attenuated virus sufficient to evoke an immune response, particularly an immune response to the protein or peptide encoded by the heterologous RNA carried by the virus, in the subject to which the virus is administered. An amount of from about 10E1 to 10E6 plaque forming units of the live virus per dose is suitable, depending upon the age and species of the subject being treated. Exemplary pharmaceutically acceptable carriers include, but are not limited to, sterile pyrogen-free water and sterile pyrogen-free physiological saline solution.

Administration of the live attenuated viruses disclosed herein may be carried out by any suitable means, including both parenteral injection (such as intraperitoneal, subcutaneous, or intramuscular injection), by in ovo injection in birds, and by topical application of the virus (typically carried in the pharmaceutical formulation) to an airway surface. Topical application of the virus to an airway surface can be carried out by intranasal administration (e.g. by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the virus as an aerosol suspension, and then causing the subject to inhale the respirable particles. Methods and apparatus for administering respirable particles of pharmaceutical formulations are well known, and any conventional technique can be employed.

In another embodiment, the present invention relates to antibodies specific for the above-described virus. For instance, an antibody can be raised against any of the viral proteins or against a portion thereof. Persons with ordinary skill in the art using standard methodology can raise monoclonal and polyclonal antibodies to a polypeptide of the present invention. Material and methods for producing antibodies are well known in the art (see for example Goding, in, Monoclonal Antibodies: Principles and Practice, Chapter 4, 1986). The antibodies can be used to monitor the presence or activity of alphaviruses and potentially as a therapeutic agent.

In a further embodiment, the present invention relates to a method of detecting the presence of EEE viral infection or antibody against this virus, if present, in a sample. Using standard methodology well known in the art, a diagnostic assay can be constructed by coating on a surface (i.e. a solid support) for example, a microtitration plate or a membrane (e.g. nitrocellulose membrane), all or a unique portion of EEE virus described above, and contacting it with the serum of a person suspected of having a viral infection. The presence of a resulting complex formed between the virus and antibodies specific therefore in the serum can be detected by any of the known methods common in the art, such as colorimetry or microscopy. This method of detection can be used, for example, for the diagnosis of EEE viral infections.

In yet another embodiment, the present invention relates to a method of detecting the presence of EEE viruses in a sample. Using standard methodology well known in the art, a diagnostic assay can be constructed by coating on a surface (i.e. solid support) for example, a microtitration plate or a membrane (e.g. nitrocellulose membrane), antibodies specific for EEE and contacting it with serum or tissue sample of a person suspected of having EEE viral infection. The presence of a resulting complex formed between virus in the serum and antibodies specific therefore can be detected by any of the known methods common in the art, such as fluorescent antibody spectroscopy or colorimetry. This method of detection can be used, for example, for the diagnosis of EEE viral infection.

In another embodiment, the present invention relates to a diagnostic kit which contains EEE virus and ancillary reagents that are well known in the art and that are suitable for use in detecting the presence of antibodies to EEE in serum or a tissue sample. Tissue samples contemplated can be obtained from birds, pigs, equines, monkeys, humans or other mammals.

In yet a further embodiment, the present invention relates to DNA or nucleotide sequences for use in detecting the presence or absence of EEE virus using the reverse transcription-polymerase chain reaction (RT-PCR). The DNA sequence of the present invention can be used to design primers which specifically bind to the viral RNA for the purpose of detecting the presence, absence, or quantization the amount of virus. The primers can be any length ranging from 7-40 nucleotides, preferably 10-15 nucleotides, most preferably 18-25 nucleotides. Reagents and controls necessary for PCR reactions are well known in the art. The amplified products can then be analyzed for the presence or absence of viral sequences, for example by gel fractionation, with or without hybridization, by radiochemistry, and immunochemical techniques.

In yet another embodiment, the present invention relates to a diagnostic kit which contains PCR primers specific for EEE and ancillary reagents that are well known in the art and that are suitable for use in detecting the presence or absence of EEE in a sample using PCR. Samples contemplated can be obtained from birds, equines, humans or other mammals. While theoretically any region in the genome can be used to make EEE primers, some non-limiting examples of specific primers are shown in FIG. 1A.

In another embodiment, the present invention relates to a method of reducing EEE viral infection symptoms in a patient by administering to said patient an effective amount of anti EEE antibodies, or protective serum from an immunized animal. When providing a patient with antibodies, the dosage or administered agent will vary depending upon such factors as the patient's age, weight, height, sex, general medical condition, previous medical history, etc. In general, it is desirable to provide the recipient with a dosage of the above compounds which is in the range from about 1 pg/kg body weight of patient; although a lower or higher dosage may be administered.

In another embodiment, the present invention relates to a method for overcoming vaccine interference in alphavirus-immune individuals. Alphavirus interference has been documented in animals and people since the 1960's. This phenomenon occurs when a live-attenuated vaccine is administered to animals or people with existing immunity to heterologous alphaviruses. Pre-existing immunity may be acquired by vaccination or infection. This presents a significant limitation to the usefulness of the current live-attenuated alphavirus vaccines, especially since the cross-reactive immunity does not protect adequately against challenge with virulent heterologous alphaviruses.

Formalin-inactivated alphavirus vaccines are not an acceptable alternative as they have significant limitations with regard to the quality and duration of protective immunity and require multiple inoculations and periodic boosters. The attenuated EEE virus vaccine of the present invention contains mutations in the viral glycoprotein sequences that may alter the sequence, conformation, and/or accessibility of cross-reactive epitopes. Alterations in epitopes that prevent binding by cross-reactive antibodies may also bypass interference in alphavirus-immune individuals. Eliminating the problem of interference would permit the EEE attenuated virus vaccine to be used in alphavirus-immune animals or people to induce protective immunity to EEE virus. Long-lasting protective immunity to both parenteral and aerosol challenge would be expected after vaccination with the live-attenuated vaccines of the present invention, and provide an additional advantage over the use of inactivated vaccines which induce short-lived responses that do not protect against mucosal challenge.

Having now described the invention, the following examples are provided to illustrate the present invention, and should not be construed as limiting thereof. In light of the present disclosure, numerous embodiments within the scope of the claims will be apparent to those of ordinary skill in the art.

Novel EEE attenuating mutations disclosed herein which may be used to carry out the present invention include deletion of five amino acids at the furin cleavage site (RRTRR) (SEQ ID NO: 2) in combination with an additional site mutation. (Please see Table A below.) Such site mutations include a substitution of arginine for histidine at codon 82 of E2 and/or deletion of the histidine codon 167 in E2. Other mutations include deletion of the five amino acids at the furin cleavage site in combination with a substitution of arginine for histidine at codon 82 of E2 and/or asparagine for serine at codon 230 of E2, and/or proline for glutamine at codon 303 of E2, and/or substitution of asparagine for isoleucine at codon 116 of E1. Other mutations include deletion of the five amino acids at the furin cleavage site in combination with a substitution of aspartic acid for alanine at codon 174 of E2, and/or asparagine for lysine at codon 186 of E2 and/or threonine for isoleucine at codon 116 of E1.

TABLE A

| EEE VaccineCandidate | Mutation(s) | In Vivo Efficacy |
|---|---|---|
| pEE4240 (Example 4) | Deleted RRTRR (SEQ ID NO: 2); D174A (E2); K186N (E2) & I116T Resulting from: Deletion of nucleotides (nt) 8552-8566 of SEQ ID NO: 1 (AGGAGAACCAGGAGA); GAC→GCC (nt9087); AAA→AAT (nt9124); ATC→ACC (nt10344) | Chickens-Sterile immunity against wt FL91 and wt South American PE-0155; Mice aerosol challenged with >1000x LD50 of wt FL91 s.c. vaccination: 100% protection i.n. vaccination: 100% protection |
| p4202RPE.40P6 (i.e. RPE.40 passage 6) | Deleted RRTRR (SEQ ID NO: 2); H82R (E2); N230S | Chickens-Sterile immunity against wt FL91 and wt |

TABLE A-continued

| EEE VaccineCandidate | Mutation(s) | In Vivo Efficacy |
|---|---|---|
| (Example 4)<br>Clone 74E2; pEE4260 | (E2); P303Q (E2) & I116N (E1)<br>Resulting from:<br>Deletion of nucleotides (nt) 8552-8566 of SEQ ID NO: 1 (AGGAGAACCAGGAGA);<br>CAT→CGT (nt8811);<br>AAC→AGC (nt9255);<br>CCA→CAA (nt9474);<br>ATC→AAT (nts10344-45) | South American PE-0155;<br>Mice aerosol challenged with >1000x LD50 of wt FL91<br>s.c. vaccination: 100% protection<br>i.n. vaccination: 100% protection |
| p4202BHKP6 (i.e. BHK passage 6)<br>(Example 4)<br>Clone 1E2deltaFurin; pEE4230 | Deleted RRTRR (SEQ ID NO: 2); H82R (E2) & deleted H167 (E2)<br>Resulting from:<br>Deletion of nucleotides 8552-8566 of SEQ ID NO: 1 (AGGAGAACCAGGAGA);<br>CAT→CGT (nt8811);<br>Deletion nts9065-9067 | Chickens-Sterile immunity against wt FL91 and wt South American PE-0155;<br>Mice aerosol challenged with >1000x LD50 of wt FL91<br>s.c. vaccination: 90% protection<br>i.n. vaccination: 20% protection |
| p4202RPE.40P3 (i.e. RPE.40 passage 3)<br>(Example 4)<br>Clone 1B7; pEE4250 | Deleted RRTRR (SEQ ID NO: 2); P303Q (E2) & I116N (E1)<br>Resulting from:<br>Deletion of nucleotides 8552-8566 of SEQ ID NO: 1 (AGGAGAACCAGGAGA);<br>CCA→CAA (nt9474);<br>ATC→AAT (nts10344-45) | Chickens-Sterile immunity against wt FL91 and wt South American PE-0155;<br>Mice aerosol challenged with >1000x LD50 of wt FL91<br>s.c. vaccination: 100% protection |
| E3 Delta3<br>(Example 5)<br>pEE2021 | Deleted CMPC (E3)<br>Resulting from:<br>Deletion of nucleotides 8438-8449.<br>Furin cleavage site intact | Chickens-Sterile immunity against wt FL91 and wt South American PE-0155;<br>Mice aerosol challenged with >1000x LD50 of wt FL91<br>s.c. vaccination: 100% protection |
| PE-6 Human Vaccine (Positive Control, 0.5 ml dose given at days 0 and 28; i.e. human vaccine regimen) | Formalin-inactivated whole virus preparation of the PE-6 strain of North American EEE. | Mice aerosol challenged with >1000x LD50 of wt FL91<br>s.c. vaccination: 80% protection |
| Small Plaque (SP) RPE.40-derived mutant<br>(Example 2) | Deleted TRR (E3); H82R (E2) & deleted H167 (E2)<br>Resulting from:<br>Deletion of nucleotides 8558-8566 (ACCAGGAGA);<br>CAT→CGT (nt8811);<br>Deletion nts9065-9067 | Chickens-Sterile immunity against wt FL91 and wt South American PE-0155;<br>Mice s.c. or i.n. challenged with >1000x LD50 of wt FL91; s.c. vaccination 0% protection |
| Large Plaque (LP)RPE.40-derived mutant<br>(Example 3) | Deleted TRR; R59S (E3); N80D (E2); H82R (E2) & deleted H167 (E2)<br>Resulting from:<br>Deletion of nucleotides 8558-8566 (ACCAGGAGA);<br>AGG→AGT (nt8554)<br>AAC→GAC (nt8804);<br>CAT→CGT (nt8811);<br>Deletion nts9065-9067 | Chickens-Sterile immunity against wt FL91 and wt South American PE-0155;<br>Mice i.n. challenged with >1000x LD50 of wt FL91<br>i.n. vaccination: 30% protection<br>s.c. vaccination: 20% protection |
| EMEM Diluent | No virus, negative control | Chickens-No immunity against wt FL91 and wt South American PE-0155 (Viremia levels at 1E5-1E6 pfu/ml blood)<br>Mice aerosol challenged with >1000x LD50 of wt FL91<br>s.c. vaccination: 0% protection<br>i.n. vaccination: 0% protection |

Explanations:
"Delete RRTRR" (SEQ ID NO: 2) = deleted furin cleavage site;
"p4202 RPE P6" = pEE4202 is parent plasmid, RPE is cell type, P6 is passage #

Additional novel EEE attenuating mutations disclosed herein which may be used to carry out the present invention include deletion of the final three amino acids at the furin cleavage site (TRR) in combination with a substitution of arginine for histidine at codon 82 of E2 and/or deletion of the histidine codon 167 in E2. Other mutations include deletion of the final three amino acids at the furin cleavage site in combination with a substitution of serine for arginine at codon 59 of E3, and/or substitution of aspartic acid for asparagine at codon 80 of E2, and/or a substitution of arginine for histidine at codon 82 of E2, and/or a deletion of the histidine codon 167 in E2.

Additional novel EEE attenuating mutations disclosed herein which may be used to carry out the present invention include deletion of the four amino acids CMPC at position 20-23 in E3.

These novel attenuating mutations may be inserted together in a cDNA clone encoding EEE virus resulting in an attenuated EEE which is reflected by 100% survival of mice inoculated by subcutaneous and intranasal routes. Such an attenuated live virus is immunogenic, safe and capable of inducing a protective effect against a lethal virus challenge.

Attenuated EEE

The following materials and methods were used in the examples that follow.

1. Viruses and Cells.

Eastern equine encephalitis virus, strain FL91-4679 (Mitchell et al., supra) was grown in baby hamster kidney (BHK) or Vero cells in Eagle's Minimum Essential Medium (EMEM) containing 10% fetal bovine serum, 200 U/ml penicillin G, 0.2 mg/ml streptomycin and 0.05 mg/ml of gentamycin. Cells were incubated at 37 C and 5% CO2.

2. cDNA Cloning.

Genomic RNA was prepared from purified virus by Trizol extraction following the manufacturer's recommended procedure. Initially, cDNA was prepared by the method of Gubler and Hoffman ([1983] Proc Natl Acad Sci. U.S.A 85:5997-6001). Subsequently, DNA representing the entire genome was prepared by polymerase chain reaction using a series of primer pairs (FIG. 1A) based upon the PE-6 genome sequence. Each PCR product was cloned into pCRII (Invitrogen). The 5' terminal sequence was determined by 5' RACE basically as described by Frohman et al. ([1988] Proc Natl Acad Sci. U.S.A. 85:8998-9002). The oligonucleotide ET7C, consisted of an Eco RI site, the promoter for bacteriophage T7 RNA polymerase followed by 18 nucleotides of the 5' terminus of FL091-4697. ET7C was paired with E1645R and used to amplify the terminal 1.6 kb of the EEE genome. The oligonucleotide E3' Not I consisted of a short EEE sequence, poly (A)21 and a Not I site. Clone pEE2002 representing the entire genome was assembled in pBluescript KS+ through the use of convenient endonuclease sites. For ease of subsequent site-directed mutagenesis of the structural protein genes, two cassettes representing the 5' terminal 7.6 kb, plasmid ERep2182, and 3' 4.2 kb, plasmid pEE.26S.F191 of the genome were prepared. Full-length clones were assembled by digestion of the ERep2182 with Cla I and Not I and insertion of a 4.1 kb Cla I/Not I fragment prepared from plasmid pEE.26S.F191 or its mutagenized derivatives.

3. Mutagenesis of the Furin Cleavage Site.

Two oligonucleotides, EEE FL d5R and EEE FL d5F, which bracket the presumed furin cleavage site [RRTRR] (SEQ ID NO: 2) located between the E3 and E2 glycoproteins were used to delete the 5 codons. Plasmid pEE.26S.F191 was used as the template for mutagenesis. EEE FL d5R and EEE FL d5F were paired with primers E6956F and E3'Not I, respectively, for 25 cycles using of PCR utilizing pEE.26S.F191 as a template. These two PCR products were then purified and added into a new PCR reaction containing primers E6956F and E3'Not1 for 30 cycles. This PCR product was then digested with Cla I and Not I and ligated into plasmid ERep2182 which had been digested with Cla I and Not I. Plasmid clones containing the furin cleavage deletion mutation were identified by Xcm I restriction endonuclease digestion due to the loss of one consensus site in the mutant sequence. The sequences of the mutations were also confirmed by sequencing. This yielded plasmid clone pEE2202 as the original full-length furin cleavage deletion mutant generated for EEE.

4. Identification of Secondary Mutations in Virus Derived from pEE2002 and pEE4202.

Virus released from cells electroporated with RNA transcribed from pEE2002 and pEE4202 were used as initial stock preparations. Supernatants from cells transfected with pEE2002 were diluted 1:30 and reintroduced into a fresh passage of furin deficient Chinese hamster ovary cells (RPE.40). The supernatant was collected when extensive cytopathic effect (CPE) was observed, typically from 3-6 days post-infection. This blind passage was continued in RPE.40 cells beyond passage 30. EEE virus derived from RPE.40 passage 9 and 23 as well as plaque isolates were concentrated through a 20% sucrose cushion and RNA isolated from the viral preparation using Trizol LS (Invitrogen). The structural genes of each mutant were amplified by reverse transcription-polymerase chain reaction amplification. The PCR products were purified (Qiagen Prep) and sequenced on an ABI-3100 Genetic Analyzer using fluorescent-tagged dideoxynucleotide terminators. Stock transfection supernatant derived from pEE4202 was similarly passaged in both RPE.40 and BHK cells. Viral isolates representing BHK passage 6 and RPE.40 passages 3 and 6 were sequenced as described previously.

5. Transcription and Transfection.

Plasmid DNA from full-length clones was digested with Not I, phenol extracted and ethanol precipitated. Typically, 0.5-1 ug of linearized DNA was transcribed in vitro by T7 RNA polymerase (Ribomax, Promega, Madison, Wis.) in the presence of 3 mM m7GpppGp (Pharmacia, Piscataway, N.J.). Electroporation of BHK cells with 0.4 ug of RNA was done as described (Pushko et al. [1995] Virology 239:389-401). The cells were then aseptically seeded into sterile T-75 tissue culture flasks with 20 ml of medium and continuously observed for CPE beginning at 24 hours post electroporation. Virus was harvested when the cells displayed significant cytopathic effect (CPE) and approximately 50% were detached from the plastic. Virus titers were determined by plaque assay on Vero cells.

Example 1

Preparation of an Infectious Clone of EEE Strain FL91-4679

The first goal of this study was to create a full-length cDNA clone of fully virulent EEE virus such that mutations leading to an attenuated phenotype could be identified. EEE strain FL91-4679 was originally chosen as the template. It was isolated from *Aedes albopictus* mosquitoes collected in Florida in 1991 (Mitchell et al., 1992). The virus has been passaged once in suckling mice, three times in Vero cells, and twice in BHK-21 cells prior to our sequencing the entire genome. It was chosen as the as the parent virus as it consistently kills 100% of C57BL6 mice when 4 logs of virus are inoculated either subcutaneously or intranasally. Since the PE-6 strain of EEE only killed 80% of mice when 8 logs were administered intraperitoneally, the PE-6 stain was overly attenuated for our purposes. Using FL91 allowed us to develop an animal model to assess the relative effects on virulence of the attenuating mutations. The sequence of the PE6 vaccine strain of EEE had been determined previously and was used as a basis for primers to prepare PCR amplification products representing the entire FL91 genome that were cloned in pCRII. Full length clones were assembled in pBluescript KS+ using convenient restriction sites as shown in FIG. 1A.

The first full-length infectious clone, pEE2002, was transcribed in vitro using T7 polymerase of Not I-linearized plasmid and the RNA transfected into BHK-21 cells. The large plaque phenotype of the resulting recombinant pEE2002 virus matched that of the parent FL-91-4679 virus. Further, SDS-PAGE analysis of the proteins constituting the recombinant wtFL91 (i.e. pEE2002) matched those of the uncloned parent FL91 virus. This is shown in FIG. 1B, lanes 1 and 3. Mice were inoculated with either the FL91-4679 parental virus or the pE2002 recombinant virus to determine relative pathogenicities. These studies indicated that the recombinant virus derived from pEE2002 had a similar pathogenicity to its parent FL91-4679. Specifically, 3 logs of pEE2002 or FL91 when administered intranasally (i.n.) resulted in 50% and 40% survival respectively, of C57Black6 mice. When 4 logs of either virus was administered i.n., 100% of mice died in both groups. When 3 logs of pEE2002 or FL91 were administered subcutaneously (s.c.), 70% and 0% of the mice challenged survived. When 4 logs of either virus was given s.c., 0% of mice challenged survived in either group.

Example 2

Initial Preparation of a Parental Cleavage Mutant of FL91

Davis et al. ([1995] Virology 212:102-110) have demonstrated that deletion of the furin cleavage site between E3 and E2 glycoproteins of Venezuelan equine encephalitis (VEE) virus is a lethal mutation. However, prolonged incubation of cells which had been transfected with RNA derived from full length clones containing the deletion, resulted in the eventual appearance of virus which was replication-competent and attenuated in mice (Davis et al., 1995, supra). Based upon a comparison of the predicted structural protein sequences of EEE and VEE, the probable cleavage site of FL91-4679 is RRTRR (SEQ ID NO: 2). The presence of the extra arginine when compared to the consensus (RX(R/K)R) alphavirus cleavage site indicated that the cleavage site of EEE virus might be more complex than that observed with VEE virus. We therefore prepared a deletion mutant in the E3-E2 cleavage site of the pEE2002 clone which lacks the five amino acids RRTRR (SEQ ID NO: 2).

Limited cytopathic effect (CPE) was observed in cells after electroporation of RNA transcribed from pEE2202; however as has been observed with both VEE and WEE furin cleavage deletion mutants the CPE was not complete. When assayed for virus by plaque formation on Vero cells, pEE2202 supernatants yielded no plaques even after extensive incubation at 37 C. Immunoflourescence analysis revealed that the EEE structural proteins were being expressed inside the transfected cells and on the cell surface. However, SDS-PAGE analysis of supernatants consistently revealed the absence of viral proteins. Further, the subsequent passage of transfection medium onto healthy monolayers did not result in any CPE indicating that cell monolayers were uninfected. For reasons unbeknownst to us at the time, virus derived from pEE2202 was incapable of budding from transfected cells.

Thus, in order to identify second site suppressor mutations necessary to resuscitate a furin cleavage deletion mutant, we designed an alternative approach. We hypothesized that by repeatedly passaging the EEE virus through furin deficient cells we could identify suppressor mutations. In effect, we postulated that we could create a transient in vitro environment in which the EEE virus would behave as if the furin site was not present. It was thought that mutations would then develop which would be identified by DNA sequencing and could be incorporated into the pEE2202 backbone. This ultimately could result in the production of the first ever resuscitated EEE furin cleavage deletion mutants. The furin deficient Chinese hamster ovary (CHO-K1) cell line RPE.40 was used in this experimental approach (Moehring and Moehring [1983] J. Biol. Chem 268: 2590-2594).

Initially, 1E7 plaque forming units (pfu) of wt virus derived from the pEE2002 infectious clone was used to infect the RPE.40 cells. When extensive CPE was evident; typically from 3-6 days post-infection (p.i.); virus was harvested. Virus was then diluted 1:30 with fresh medium and added to a healthy tissue flask. The propagated virus quickly diminished to low levels, the titer at passage four was 5.0E2 plaque forming units per milliliter (pfu/ml) of culture supernatant. (Please see FIG. 9.) At passage six, plaques became evident on the cell monolayer. By passage nine, EEE viral titers had recovered to high levels and had plateaued around 2E7 pfu/ml. During this period we observed a complete shift from the large plaque wt phenotype to a significantly smaller plaque phenotype. This change is usually indicative of an attenuated alphavirus.

Sequencing of the mutant virus from RPE.40 passage 9 revealed nine nucleotides (8558-8566) were deleted which encoded the E3 carboxyl terminus of E3 and the EEE furin cleavage site (Please see Table A, Small Plaque RPE.40-derived Mutant). In effect, the furin cleavage site had mutated from RRTRR (SEQ ID NO: 2) into RR---, where - represents a deletion. Coomassie blue stained polyacrylamide gels revealed that the mutant virus was composed solely of PE2 protein and the normal E2 protein band was absent. This would be expected if the normal furin cleavage was interrupted. Two additional second site mutations were identified in the structural gene encoding the E2 glycoprotein. The first involved a single nucleotide change which resulted in a substitution of arginine for histidine at E2 amino acid 82. The other RPE.40-derived mutation resulted in a deletion of 3 nucleotides which resulted in the loss of the histidine codon at E2 amino acid 167. (For a summary please see Small Plaque RPE.40-derived mutant EEE listed in Table A). These mutations were also evident in two separate plaque isolates from RPE.40 passage nine and RPE.40 passage 23. This latter result suggests that the mutant genome derived by RPE.40 serial passage is stable. Since this mutant EEE derived from RPE.40 passage lacked a functional furin cleavage site we elected to test the virus for efficacy in vivo.

Mutant EEE derived from RPE.40 passage nine was first tested for attenuation and protective effect in birds. Specifically, one-day-old leghorn chickens were subcutaneously (s.c.) inoculated with the mutant virus and a control group received the wt FL91 virus. The positive control group became moribund within 24 hours post-infection (p.i.). Further, the animals developed a significant viremia prior to being euthanized. The EEE virus was titered at 1E9-1E10 plaque forming units (pfu) per milliliter (ml) of blood (abbreviated pfu/ml from here on). The chicks inoculated with the mutant EEEs also developed a viremia though at its zenith on day 3 was only 1E4 pfu/ml. All birds receiving the mutant EEE survived and there were no signs of illness, indicating that the mutant virus was fully attenuated in vivo. Fourteen days post-vaccination birds were challenged s.c. with the parent wt FL91 virus. All birds previously inoculated with the mutant EEE exhibited no viremia (0 pfu/ml, sterile immunity) while naïve, unvaccinated birds developed a viremia from 1E5-1E6 pfu/ml. This result is indicative that the RPE.40- derived mutant EEE provided protection against a North American EEE. For a summary of the efficacy results please see Small Plaque (SP) RPE.40-derived mutant EEE listed in Table A.

The protection we observed against North American EEE was not construed as an indication that the mutant EEE could protect against South American EEE. Previous work of others (Strizki et al. [1995] Am. J. Trop. Med. Hyg. 53: 564-570) has shown that the PE-6 IND EEE vaccine provides inadequate protection against antigenically distinct South American EEE strains. These antigenically distinct EEE strains exhibit significant serologic and molecular differences from their North American counterparts (Brault et al. [1999] Am. J. Trop. Med. Hyg. 61: 579-586; Weaver et al. [1994] J. Virology 68: 158-169). Aware of this shortcoming, we examined whether the RPE.40-derived mutant EEE could provide protection against a South American EEE strain. Identical experiments in birds to those previously described were conducted, except the birds were challenged with South American EEE strain PE-0155 (Turell, USAMRIID unpublished data; isolated from an infected *Culex pedroi* mosquito in 1996 at Puerto Almendras, Loreto Department, Peru). Similar efficacy results were obtained, protection was clearly observed against this South American EEE. Unvaccinated birds at day 3 post-challenge had developed a viremia from 1E5-1E6 pfu/ml, while no viremia (0 pfu/ml, sterile immunity) was evident in any of the birds pre-inoculated with the mutant EEE. This protection to a strain of South American EEE is an added bonus to developing live, attenuated viruses as the next generation EEE vaccine. The PE-6 inactive vaccine does not provide protection against South American EEEs (Strizki et al. supra). A full-length molecular clone was made that represented this mutant (Small plaque RPE.40-derived mutant contained the partial furin cleavage deletion mutation (loss of TRR), H82R and the deleted histidine 167 codon. Recombinant virus derived from this clone behaved similarly to the parent RPE.40-derived small plaque (SP) biological isolate. This efficacy data is summarized in Table A.

We next examined efficacy in a mammalian animal model. Balb/c mice were s.c. inoculated and as in birds all survived indicating the mutant virus was fully attenuated. When mice received an s.c. lethal challenge at day 42 post-vaccination, no protection was observed. The immunized mice died at similar times to the control group that received EMEM medium alone. Analysis of serum samples from inoculated mice indicated EEE-specific neutralizing antibodies were absent. Hence, for our ultimate purpose the small plaque RPE.40-derived mutant EEE was overly attenuated. In order to study a more robust mutant, we revisited the earlier bird studies.

Example 3

Preparation of a More Robust Partial Furin Cleavage Mutant of FL91

Since the original RPE.40-derived mutant EEE was overly attenuated we next generated a more robust mutant virus. We had previously observed that day-3 post-immunized viremic bird blood contained both small-plaques (SP) similar to the parent RPE.40-derived EEE as well as a larger plaque (LP) phenotype. It seemed conceivable that these LP mutants could be less attenuated than the parent based on previously published data on Sindbis alphavirus mutants (Byrnes et al. [2000] J. Virology 74: 644-651). They observed that when attenuated small plaque Sindbis mutants were inoculated into mice, larger plaque mutants developed. More importantly, reintroduction of the LP Sindbis mutants back into mice revealed that the LP mutants had a significantly longer circulatory half life than the parental SP mutant. This property would be of value to an EEE vaccine candidate as it could allow the organism to mount a more robust immune response. Consequently, several large plaque EEE mutants were isolated and expanded in BHK cells. Viral titers determined on Vero cells were consistently from 5-15-fold higher than the parental SP. The LP isolate with the highest titer was characterized further. Viral RNA was isolated, cDNA produced and PCR products were generated that permitted complete sequencing of the structural gene region. All of the original mutations were present in addition to two others. The E3 C-terminus was modified from CNARR--- (SEQ ID NO: 3) to CNASR--- (SEQ ID NO: 4), due a single nucleotide mutation. This resulted in a new glycosylation site adjacent to where the furin cleavage site was originally located. A shift to a higher molecular weight PE2 in stained polyacrylamide gels implies that the new glycosylation site is utilized. The other mutation was due to a single nucleotide change that altered the amino acid at position 80 of E2 from asparagine to an aspartic acid (AAC to GAC). No mutations were observed in the capsid, 6K, E1 or the 3' UTR. This LP phenotype is due solely to these mutations in E3 and E2 since a recombinant virus produced from a molecular clone containing only these mutations behaved similarly to its LP parent. This is identified as the Large Plaque RPE.40-derived mutant in Table A.

This LP mutant EEE was tested for efficacy in mice following the procedures described previously. All mice survived subcutaneous (s.c.) and intranasal (i.n.) inoculation of the LP vaccine candidate. There were no signs of illness indicating the virus was fully attenuated. However, unlike its SP parent, the LP EEE mutant provided partial protection in the Balb/c mouse model against both a lethal intranasal challenge (30%) and s.c. challenge (20%). A similar i.n. dose (1E4 plaque forming units) of the EEE mutant parent SP provided no protection. This SP result in conjunction with the surviving LP-inoculated mice having significant neutralizing antibody responses [≧1:40] indicated that the additional two genomic mutations made the LP mutant virus less attenuated. Studies were also conducted in 1-3-day-old leghorn chickens following the procedure described previously in example 2. The LP EEE mutant was fully attenuated when s.c. inoculated into birds. Further, this LP mutant provided complete protection (0 pfu/ml) against both the FL91 North American EEE and the PE-0155 South American EEE. Naïve challenged birds developed a 1E5-1E6 pfu/ml viremia.

Example 4

Molecularly-Derived Full-Length Furin Cleavage Deletion Mutants of FL91

The final tier of experiment focused on the production of viable, infectious virus from the furin-cleavage deletion mutant. This approach has been used successfully to produce vaccine candidates for both VEE (Hart et al., [2000] Vaccine 18: 3067-3075; Pratt et al., [2003] Vaccine 21: 3584-3862) and WEE (Turell et al., [2003] Am J Trop Med Hyg 68: 218-221). One VEE vaccine candidate, V3526, has been approved by the FDA for phase I clinical trials.

In order to address why the full-length furin-cleavage deletion clone pEE2202 was incapable of producing virus, we elected to sequence the entire genome of FL91-4679. We suspected that the clone contained deleterious mutations derived from the original PCR process used to make the clone. The entire 11,681 nucleotide FL91-4679 genome was sequenced (Sequence attached SEQ ID NO: 1). Comparison of the nascent viral sequence to that of the resequenced full-length clone pEE2002 revealed 2 single nucleotide mutations within the structural region that resulted in non-conservative amino acid changes. Specifically, these changes resulted in a tyrosine153cysteine (E2; TAC→TGC nucleotide 9024) and arginine204cysteine (E1; CGC→TGC nucleotide 10616) mutation. These two mutations were thought to have had a negative impact on the production of furin cleavage deletion mutant virus. Several other mutations were also identified in the nonstructural region but were not considered to be as deleterious as the cystiene point mutations found in E1 and E2.

Consequently, these two deleterious mutations were replaced with the nascent FL91 sequence. A PCR product was generated using primers E8275F (see FIG. 1A) and E3'Not I and the wt FL91 virus as template. The amplification product was digested with Eco RI/Not I and subcloned into the pEE2002 plasmid. This resulted in the production of the second generation EEE infectious clone termed, pEE4002. This new plasmid was fully sequenced which ensured the absence of any further mutations. A new furin cleavage mutant clone, pEE4202, was made using this new infectious clone as a platform. Specifically, an Nco I/Eco RI fragment from pEE2202 was subcloned into the pEE4002 to produce the new furin cleavage deletion plasmid pEE4202. Infectious RNA was generated from Not I-linearized pEE4202 and transfected into BHK cells by electroporation. Extensive cytopathic effect (CPE) was observed several days post-transfection illustrating that pEE4202 could produce infectious virus that lacked a furin cleavage site (Please see FIG. 1B). This recombinant EEE virus plaqued significantly smaller than the wild-type parent as was observed with the V3526 furin cleavage mutant. Additionally, virus from the pEE4202 transfection had a very low titer on Vero cells, around 1E4 pfu/ml (See FIG. 9). An acceptable titer for virus vaccine production is approximately 1E6 pfu/ml taking into consideration the challenges of production scale-up.

Thus, to achieve higher titer pEE4202 stock virus, the transfection supernatant was serially passaged through two separate cell lines, RPE.40 (CHO-K1 cells deficient in the furin protease; Moehring and Moehring[1983] supra) and baby hamster kidney (BHK) cells (contains a functional furin protease). This resulted in the generation of EEE furin cleavage deletion mutant virus at significantly higher titers (>1E7 pfu/ml) and permitted us to conduct in vivo efficacy studies. In addition, the selective pressure imposed by the two different cell lines resulted in two different sets of second site mutations. Virus derived from pEE4202 passaged six times through BHK cells (i.e. p4202BHKP6, Table A) contained the furin cleavage deletion in addition to the two previously cell culture-derived E2 mutations. Specifically, mutations found in p4202BHKP6 involved H82R and the deletion of amino acid Histidine 167. Virus from RPE.40 passage 3 contained the furin cleavage deletion in addition to a glutamine to proline mutation at amino acid 303 of E2 and an isoleucine to asparagine change at amino acid 116 of the E1 glycoprotein (called p4202RPE.40P3, Table A). Sequence analysis of RPE.40 passage 6 virus revealed the same mutations observed in RPE.40 passage 3 in addition to an H82R and an asparagine to serine substitution at amino acid 230 in E2 (called p4202RPE.40P6, Table A). These three furin cleavage deletion mutants were tested for efficacy in birds and mice.

In addition to these three mutants, clone pEE4240 was also tested for efficacy in vivo. This EEE furin cleavage deletion mutant contained three second site mutations identified by repeated serial passage of the uncloned wild type FL91 virus through RPE.40 cells (please see Table A). These mutations included an aspartic acid to alanine change at position 174 of E2, a lysine to asparagine substitution at position 186 of E2 and an isoleucine to threonine change at position 116 of E1. The lysine to asparagine mutation resulted in the generation of a putative N-linked glycosylation site in E2. SDS-PAGE analysis of the purified virus indicates that carbohydrate is present at this location. All three of these unique second site mutations were incorporated into the furin cleavage deletion mutant, pEE4202 to make pEE4240. Please see data table A for a summary of these vaccine candidates.

These four EEE furin cleavage deletion viruses were tested in vivo to determine if they could elicit a protective immune response against the lethal parent FL91. Each virus was subcutaneously inoculated into a group of 1-day-old Leghorn chickens. Simultaneously another group received the parent wt FL91 control. Birds receiving the vaccine candidates developed a short, limited viremia no higher than 1E4 pfu/ml. Naïve birds receiving the virulent parent developed a significant viremia (>1E9 pfu/ml) and by 24 hours post-infection became moribund or had perished. All birds receiving EEE vaccine candidates survived, none exhibited any signs of sickness. This clearly indicated that each of the four viral candidates was attenuated in vivo. Fourteen days post-vaccination birds were challenged s.c. with the virulent FL91 parent along with a control group of naïve birds. All control birds developed a mild viremia (1E5-1E6 pfu/ml) while all previously vaccinated birds showed no signs of viremia (0 pfu/ml). This is indicative that the vaccine candidates provided complete protection against the parent North American FL91 virus. Additionally, pre-challenge serum from vaccinated birds contained EEE-specific neutralizing antibodies. The attenuated viruses had elicited the production of a significant humoral immune response which is a known correlate to alphavirus immunity.

The protective effect we observed against a North American EEE for these vaccine candidates was not considered to imply that there would be protection against antigenically distinct South American EEEs. To determine if these four vaccine candidates were capable of this broad protection, similar bird experiments to those described above were repeated but the challenge was with South American strain PE-0155 (Turell, unpublished data; isolated from an infected *Culex pedroi* mosquito in 1996 at Puerto Almendras, Loreto Department, Peru). Similar to the previous result, each of the vaccine candidates provided complete immunity (0 pfu/ml) to this South American strain whereas control birds developed a viremia from 1E5-1E6 pfu/ml. This protection against both North and South American EEEs was directly attributed to the live, attenuated vaccine candidates. Work by others (Strizki, et al, [1995] supra) has shown that the PE-6 EEE inactive vaccine provides inadequate protection against antigenically distinct South American EEE strains. Thus, the fact that these live, attenuated mutants were capable of protecting birds against South American EEE is a crucial property in the development of a new EEE vaccine. These vaccine candidates can potentially be used to protect animals and humans against the array of EEEs which exist in South America and are often transported to the U.S. through migratory birds.

TABLE B

Mouse Examples 4 & 5 Data Summary/EEE Aerosol Challenge

| Group | Vaccine | Dose (pfu) | Survived/Tested | Serum Neutral Antibodies |
|---|---|---|---|---|
| 1 | pEE4240 | 2.05E6 | 10/10 | + |
| 2 | p4202RPE40P6 | 5.24E6 | 10/10 | + |
| 3 | p4202BHKP6 | 8.70E5 | 9/10 | + |
| 4 | p4202RPE40P3 | 8.70E6 | 10/10 | + |
| 5 | E3Delta3 | 1.9E7 | 10/10 | + |
| 6 | PE6 IND* | Inactivex2 | 8/10 | + |
| 7 | Medium | N/A | 0/10 | − | s.c. vaccine x1 in 4-8 week old balb/c mice
*PE6 IND inactive vaccine given s.c. day 0, day 28
Pre-bleeds at Day 35, Aerosol challenge with WtFL91 (>1000x LD50) at Day 42

We next tested each of these four vaccine candidates in mice to determine if they could elicit a protective effect in mammals. Each candidates was inoculated s.c. into 4-8 week Balb/c mice. Positive control group mice received the human IND vaccine regime of the PE-6 formulation at day 0 and day 28 (i.e. 0.5 ml×2 s.c. inoculations). The negative control group mice received sterile EMEM media diluent. All mice receiving the vaccine candidates exhibited no signs of sickness indicating that the viruses were attenuated in vivo. At day 35 post-vaccination a limited volume of serum was acquired from mice for antibody analysis. At day 42 post-vaccination mice received a lethal, aerosol challenge of the virulent parent, wt FL91 that was greater than 100×LD50. All of the mice receiving the viral vaccine candidates pEE4240, p4202RPE.40P3 or p4202RPE.40P6 survived. Nine of the ten mice that received the p4202BHKP6 virus survived. Eight of the ten mice receiving the human vaccine regime of PE-6 survived. None of the negative control, naïve mice survived (Table B). Each of the four live, attenuated vaccine candidates tested provided better protection than the currently used PE-6 vaccine. Clearly, the live, attenuated vaccine candidates provided better protection that the inactive vaccine preparation. This is quite remarkable considering that the mice received two 0.5 ml doses of the PE-6 vaccine (i.e. human vaccine dose regime) compared to one diluted 0.2 ml s.c. inoculation of the candidates. All of the surviving mice exhibited a significant neutralizing antibody response specific to EEE.

TABLE C

Mouse Examples 4 & 5 Intranasal Inoculation Safety Data Summary

| Group | Vaccine | Intranasal Dose (pfu) | Survived/Tested |
|---|---|---|---|
| 1. | pEE4204 | 2.05E5 | 10/10 |
| 2. | p4202RPE40P6 | 5.24E5 | 10/10 |
| 3. | p4202BHKP6 | 8.70E4 | 10/10 |
| 4. | E3Delta3 | 1.90E6 | 0/10* |
| 5. | Medium | 20 μL | 10/10 | i.n. vaccine x1 in 4-8 week old balb/c mice
Pre-bleeds at Day 35
*Delayed mean time of death relative to control mice

TABLE D

Mouse Example 4 Intranasal Data Summary/EEE Aerosol Challenge

| Group | Vaccine | Survived/Tested | Serum Neutralizing Antibodies |
|---|---|---|---|
| 1. | pEE4240 | 10/10 | ++ |
| 2. | p4202RPE40P6 | 10/10 | +++ |
| 3. | p4202BHKP6 | 2/10 | + |
| 4. | Medium | 0/10 | − | i.n. vaccine x1 in 4-8 week old balb/c mice
Pre-bleeds at Day 35
Aerosol challenge with WtFL91 EEE (≧1000x LD50) at Day 42

We next sought to determine if the vaccine candidates were safe (i.e. lacked neurovirulence). EEE vaccine candidates pEE4240, p4202.RPE.40P6 and p4202.BHKP6 were intranasally (i.n.) administered into 4-8 week Balb/c mice. All of the mice receiving the vaccine candidates survived with no signs of illness indicating that the mutant viruses lacked neurovirulence (Table C). Zero out of the ten control mice receiving the wt FL91 virus i.n. survived, the mean day of death was 5.2 days. We next tested whether this single intranasal inoculation of the vaccine candidates was sufficient to provide protection. Forty-two days post i.n. vaccination, mice were subjected to a >1,000×LD50 lethal aerosol challenge with parent wt FL91. All mice receiving either pEE4240 or p4202.RPE.40P6 survived indicating that these candidates can provide immunity even when 0.02 ml was administered i.n (Table D). Only two of ten mice that received the p4202.BHKP6 mutant virus survived aerosol challenge. This candidate is apparently less efficacious than p4EE4240 and p4202.RPE.40P6. All of the naïve mice that received EMEM medium perished shortly after aerosol challenge.

Furin cleavage deletion molecular clones have been generated that represented the mutant viruses derived from pEE4202 BHK Passage 6 and RPE.40 Passages 3 and 6. They are called pEE4230, pEE4250 and pEE4260, respectively. Each of these recombinant viruses behaved similarly to their parent biological isolate. Variations in the non-structural region may occur but will not significantly impact the efficacy of the vaccine candidate.

This study represents the first time that live, attenuated mutant EEEs have been produced that are capable of providing 100% protection against lethal aerosol challenges. Further, we have made defined molecular clones for each vaccine candidate which permits us to easily produce significant amounts of the recombinant viruses.

Example 5

Molecularly Derived Attenuated Mutant with an Intact Furin Cleavage Site

An alternative deletional approach to create EEE vaccine candidates was also examined. Specifically, rather than deleting the furin protease cleavage site, a small region of E3 was removed by site directed mutagenesis. Twelve nucleotides were deleted and the furin cleavage site was kept intact (Please see Table A, E3Delta3). These deleted nucleotides code for E3 residues 21-24 that represent cystiene-methionine-proline-cystiene. This short sequence is unique to EEE relative to the other New World alphaviruses VEE and WEE. This molecular clone termed E3 Delta 3 (also called pEE2021) was made by 2-stage PCR site-directed mutagenesis using the procedures previously described to make EEE molecular clones. Two primers were produced to create the mutation. They were E3Delta3 5F and E3Delta3 6R. The sequence for each listed 5' to 3' is listed below.

E3D3 5F

5' TTTCCATGTGATCAACACCCTGTTATGAAAAGAATCCACACGA 3'   (SEQ ID NO: 5)

E3D3 6R

5' TCGTGTGGATTCTTTTCATAACAGGGTGGTTGATCACATGGAAA 3'   (SEQ ID NO: 6)

The final plasmid construct has an intact furin site and used the pEE2002 plasmid as the parent backbone. Commassie blue stained SDS-PAGE gels revealed that the purified E3Delta3 virion contained E2 and not PE2 indicating furin cleavage occurs. Analysis of similar gels with silver stain revealed that the E3Delata3 mutant lacked the E3 protein that is normally found in the wtFL91 virion (unpublished results).

When the E3Delta3 mutant was administered subcutaneously into birds or mice all survived with no signs of illness indicating the mutant was highly attenuated. As was observed previously, birds inoculated with E3Delta3 (also called pEE2021) were protected against both a North and South American strain of EEE. No viremia was evident in vaccinated bird serum (0 pfu/ml) whereas control bird serum exhibited a viremia from 1E5-1E6 pfu/ml. All mice inoculated s.c. with this candidate survived a lethal aerosol challenge 42 days post-vaccination (Please see Table A). When the mutant was administered intranasally, all of the Balb/c mice perished. Unfortunately, this mutant still contains some level of neurovirulence though the average time of death (8.9 days) was substantially delayed relative to the wt FL91 (5.2 days). This is the first time that a non-furin cleavage deletion New World alphavirus mutant was shown to be completely efficacious against a lethal aerosol challenge. This experiment clearly shows that a variety of other genome deletional approaches could possibly be used to produce attenuated viruses that have the potential to become vaccines.

Preparation of a Vaccine:

A vaccine can be prepared that contains one suppressor mutation or multiple suppressor mutations. Further, a vaccine can be prepared that contains one candidate or multiple candidates in a single vaccine. It is preferable to deliver the vaccine subcutaneously, however many other routes are also acceptable (intranasal, intradermal, etc.). Carriers include but are not limited to saline, PBS, sterile water and an aerosol spray. Adjuvants have also been contemplated, such as, for example Freund's or other adjuvants known in the art.

The sequence of pEE4002 is the same as wild type FL-91, with the exception of several mutations in the nonstructural region.

Sequence for FL-91

ATAGGGTACGGTGTAGAGGCAACCACCCTATTTCCACCTATCCAAAATGGAG    (SEQ. ID. NO: 1)
AAAGTTCATGTTGACTTAGACGCAGACAGCCCATTCGTCAAGTCACTGCAAA
GATGCTTTCCACATTTTGAGATAGAAGCAACGCAGGTCACTGACAATGACCA
TGCTAATGCTAGGGCGTTTTCGCACCTAGCTACTAAGCTCATTGAGGGAGAA
GTGGATACAGACCAGGTGATCCTGGATATTGGGAGCGCGCCTGTAAGGCACA
CGCATTCCAAACATAAGTACCACTGTATTTGCCCAATGAAGAGCGCAGAAGA
CCCTGACAGACTCTACCGCTACGCAGACAAGCTTAGAAAGAGTGATGTCACT
GACAAATGTATTGCCTCTAAGGCCGCGGACCTGCTAACAGTAATGTCGACGC
CCGACGCTGAGACACCCTCGTTATGCATGCACACTGACTCAACTTGCAGGTA
CCACGGCTCCGTGGCCGTATATCAGGATGTATATGCAGTGCATGCACCGACTT
CCATTTACTACCAGGCGCTGAAAGGTGTACGAACTATCTATTGGATCGGGTTC
GATACTACACCGTTCATGTATAAGAACATGGCAGGCGCCTACCCTACATACA
ACACTAATTGGGCCGATGAAAGTGTGTTGGAAGCCAGAAATATAGGGCTGGG
TAGTTCAGACTTGCACGAAAAGAGTTTCGGAAAAGTATCCATTATGAGGAAG
AAGAAATTACAACCCACCAATAAAGTAATATTTTCTGTGGGGTCAACTATTTA
TACTGAAGAGAGAATACTGTTACGCAGTTGGCATCTACCTAATGTTTTTCATC
TAAAAGGTAAAACTAGCTTTACAGGCAGATGTAACACTATCGTCAGCTGCGA
AGGTTACGTTGTCAAGAAGATTACGCTTAGTCCTGGGATTTACGGGAAAGTG
GATAATCTTGCTTCGACCATGCACCGAGAGGGATTCTTAAGTTGCAAGGTTAC
AGATACGTTAAGAGGGGAGAGGGTCTCTTTTCCCGTGTGTACGTACG
TGCCAGCGACACTGTGCGACCAGATGACCGGGATACTGGCGACTGACGTCAG
TGTCGATGACGCCCAGAAGCTGCTGGTTGGGCTCAACCAGCGAATTGTCGTC
AATGGCAGAACACAACGTAACACAAATACCATGCAGAATTATCTATTACCAG
TGGTCGCCCAGGCGTTCTCGCGGTGGGCGCGGGAACACCGCGCAGACCTGGA
GGACGAAAAAGGGCTAGGGGTACGGGAACGTTCCCTAGTCATGGGCTGCTGC
TGGGCTTTCAAAACTCACAAGATCACATCCATTTACAAGAGACCTGGGACTC

-continued

Sequence for FL-91

AAACTATCAAGAAGGTGCCCGCCGTATTCAATTCCTTTGTCATCCCACAACCA
ACCAGCTATGGGCTTGATATAGGATTGCGTCGCCGAATTAAGATGCTATTCG
ACGCAAAGAAGGCACCCGCTCCAATTATTACTGAGGCCGACGTTGCACACCT
TAAAGGCCTGCAGGATGAAGCTGAAGCCGTGGCTGAGGCTGAAGCCGTACGT
GCAGCACTACCTCCACTTCTGCCGGAGGTCGACAAGGAGACCGTAGAGGCTG
ACATCGACCTGATCATGCAGGAGGCAGGAGCAGGCAGCGTGGAGACACCTA
GACGACACATCAAGGTCACGACGTACCCAGGAGAAGAAATGATCGGCTCGT
ACGCAGTGCTTTCACCACAAGCGGTCCTTAACAGCGAGAAGCTCGCTTGTATT
CACCCGTTAGCTGAGCAAGTGCTCGTGATGACTCACAAAGGGCGCGCAGGAC
GATACAAGGTAGAGCCATACCACGGTAGAGTTATCGTCCCTAGTGGTACAGC
TATACCAATCCTCGATTTCCAGGCTCTGAGTGAAAGTGCAACCATAGTATTTA
ACGAACGGGAGTTCGTTAACCGTTACTTACACCACATTGCCGTTAACGGAGG
GGCACTGAATACAGATGAAGAGTACTACAAGGTTGTGAAAAGCACTGAGAC
AGACTCTGAGTACGTATTTGACATCGACGCAAAGAAGTGCGTAAAGAAAGGG
GATGCCGGACCAATGTGCCTGGTCGGCGAATTAGTAGACCCGCCATTCCACG
AATTTGCGTACGAGAGTTTAAAAACACGTCCTGCTGCACCACACAAAGTGCC
TACCATCGGAGTTTATGGAGTCCCAGGTTCCGGAAAGTCTGGTATAATCAAA
AGCGCTGTTACCAAACGTGATCTGGTGGTCAGTGCAAAGAAAGAAAATTGCA
TGGAAATCATTAAAGACGTCAAACGTATGCGCGGCATGGACATCGCCGCCCG
CACAGTGGATTCGGTGCTGCTAAATGGGGTAAAACACTCCGTCGACACACTG
TACATAGACGAGGCATTCGCTTGCCATGCAGGGACCCTGCTAGCACTTATTGC
CATCGTCAAGCCAAAGAAAGTTGTATTGTGTGGAGATCCGAAACAATGCGGC
TTCTTTAACATGATGTGTCTAAAAGTGCATTTTAACCACGAGATATGCACAGA
AGTGTATCACAAGAGTATTTCTCGGCGATGCACTAAGACAGTGACATCCATC
GTTTCCACCCTGTTCTATGATAAACGGATGAGAACTGTCAACCCATGCAATGA
TAAGATCATAATAGATACCACCAGTACTACCAAACCTTTAAAGGATGACATA
ATATTAACCTGCTTTAGAGGGTGGGTTAAACAACTGCAGATTGACTACAAGA
ACCACGAGATCATGACTGCAGCGGCCTCACAGGGGCTTACTAGAAAAGGGGT
ATACGCAGTGCGCTACAAGGTCAATGAGAACCCACTATACGCACAGACATCT
GAGCATGTGAATGTATTACTTACACGCACTGAAAAACGTATAGTATGGAAGA
CTTTGGCCGGTGACCCTTGGATCAAGACGTTGACAGCATCGTATC
CGGGTAATTTCACCGCCACACTGGAAGAATGGCAAGCTGAGCATGACGCTAT
CATGGCGAAAATACTTGAGACACCAGCTAGCAGCGACGTTTTCCAAAATAAA
GTGAACGTCTGCTGGGCCAAAGCGCTAGAACCTGTGTTGGCCACCGCCAATA
TTACGCTGACCCGCTCGCAGTGGGAGACTATTCCAGCGTTCAAGGATGACAA
AGCGTATTCGCCTGAGATGGCCTTAAACTTTTTCTGCACCAGATTCTTTGGCG
TCGACATCGACAGCGGGTTGTTCTCCGCGCCAACTGTTCCGCTGACTTACACC
AATGAACACTGGGATAATAGCCCAGGTCCAAACATGTATGGTTTGTGCATGC

Sequence for FL-91

```
GCACTGCTAAAGAACTTGCACGTCGGTATCCTTGTATTCTGAAAGCCGTGGAT
ACAGGTAGAGTGGCTGACGTTCGCACAGACACTATCAAAGACTATAACCCGC
TAATAAATGTGGTACCCTTGAATAGAAGACTCCCACACTCATTGGTTGTCACA
CATAGATACACTGGGAACGGTGATTACTCCCAGCTAGTGACCAAGATGACCG
GAAAAACCGTACTAGTAGTGGGTACACCTATGAACATACCAGGAAAGAGAG
TCGAGACACTAGGCCCAAGCCCACAATGTACATATAAAGCGGAACTGGACCT
GGGCATTCCTGCCGCTTTAGGCAAATATGACATCATTTTTATTAACGTGAGGA
CTCCCTACCGACACCACCATTACCAACAGTGCGAGGACCATGCGATCCACCA
CAGCATGCTTACCAGAAAAGCAGTGGACCATTTGAACAAAGGCGGTACGTGC
ATCGCATTGGGCTATGGGACTGCGGACAGAGCCACCGAGAACAT
TATCTCTGCAGTCGCCCGCTCATTCAGGTTCTCACGTGTGTGCCAGCCGAAGT
GTGCCTGGGAAAACACTGAGGTCGCGT
TCGTGTTTTTCGGCAAGGACAACGGCAACCATCTCCAAGATCAAGACAGGCT
GAGTGTTGTGTTAAACAACATATACCAA
GGGTCAACTCAACATGAAGCTGGCAGAGCACCTGCGTATAGAGTGGTGCGCG
GTGACATAACAAAGAGCAATGATGAGGT
TATTGTTAACGCGGCGAACAACAAAGGGCAACCCGGTAGCGGTGTGTGTGGC
GCCCTTTACAGGAAGTGGCCTGGAGCTT
TTGATAAGCAGCCGGTAGCAACTGGTAAAGCGCACCTCGTCAAGCATTCTCC
GAACGTCATCCATGCCGTTGGCCCTAAT
TTTTCTCGGCTATCAGAAAACGAAGGAGACCAGAAATTGTCTGAAGTGTACA
TGGACATTGCCAGAATTATCAACAACGA
GAGGTTTACTAAAGTCTCCATTCCGTTGTTATCTACCGGCATCTACGCAGGTG
GTAAGGACAGGGTTATGCAATCGCTGA
ACCATTTATTTACAGCCATGGATACTACCGACGCAGACATTACTATTTACTGT
CTAGATAAGCAATGGGAGTCAAGAATA
AAGGAAGCTATCACTCGGAAGGAAAGCGTTGAAGAGCTTACTGAGGATGAC
AGACCAGTTGACATTGAACTGGTACGGGT
GCACCCGTTGAGCAGCTTGGCAGGTAGACCTGGTTATTCAACCACCGAGGGC
AAGGTGTATTCGTACCTAGAGGGGACTA
GGTTTCATCAAACTGCCAAAGACATAGCTGAAATTTACGCTATGTGGCCTAA
CAAGCAAGAAGCAAACGAGCAGATTTGC
TTATACGTGTTGGGAGAGAGTATGAACAGCATCCGCTCTAAGTGTCCAGTTG
AAGAGTCGGAGGCCTCTTCCCCCCCTCA
CACCATCCCGTGTCTGTGCAACTATGCAATGACTGCAGAGCGAGTTTACAGA
TTACGTATGGCAAAGAATGAACAATTCG
CAGTTTGTTCGTCCTTTCAGTTACCGAAATACAGGATTACAGGGGTTCAGAAA
ATTCAATGCAGTAAACCTGTGATATTC
```

-continued

Sequence for FL-91

TCTGGCACTGTACCCCCGGCCATACATCCAAGAAAATTCGCATCTGTGACAG
TGGAAGACACTCCGGTGGTCCAACCTGA
AAGGTTGGTGCCTAGGCGACCTGCACCGCCTGTGCCCGTACCTGCAAGAATC
CCCAGCCCTCCATGTACATCGACCAACG
GATCGACGACCAGTATACAATCACTGGGGGAGGATCAAAGCGCATCTGCTTC
TAGCGGAGCTGAAATCTCTGTAGACCAG
GTTTCGCTATGGAGCATACCCAGCGCTACTGGGTTCGATGTGCGTACCTCCTC
ATCGTTGAGTCTAGAGCAGCCTACCTT
TCCGACAATGGTTGTCGAAGCAGAGATTCACGCCAGTCAAGGATCACTGTGG
AGCATACCCAGTATCACCGGATCTGAAA
CCCGTGCTCCGTCACCTCCAAGTCAGGATAGTAGACCTTCCACCCCATCTGCA
AGTGGTTCACACACGTCCGTGGACTTA
ATCACGTTTGACAGCGTTGCAGAGATTTTGGAGGATTTCAGTCGTTCGCCGTT
TCAATTTTTGTCTGAAATCAAACCTAT
TCCTGCACCTCGTACCCGAGTTAATAACATGAGCCGCAGCGCAGACACGATC
AAACCAATTCCAAAGCCGCGTAAATGCC
AGGTGAAGTACACGCAGCCACCTGGCGTCGCCAGGGTCATATCGGCAGCGGA
ATTTGACGAGTTTGTGCGGAGGCACTCG
AATTGACGGTACGAAGCGGGCGCGTACATTTTCTCATCCGAGACGGGACAAG
GGCACCTGCAACAAAAATCTACGCGGCA
ATGCAAACTCCAGTATCCAATCCTGGAGCGTTCCGTCCATGAGAAATTTTACG
CCCCGCGCCTCGATCTCGAGCGTGAGA
AGCTGTTGCAGAAGAAACTACAATTGTGTGCTTCTGAAGGTAATCGGAGCAG
GTATCAGTCTCGTAAAGTAGAGAACATG
AAGGCAATCACCGTTGAGCGTCTACTGCAGGGGATAGGCTCATACCTCTCTG
CAGAACCGCAACCAGTTGAATGCTACAA
AGTCACCTATCCTGCTCCCATGTATTCAAGTACTGCAAGCAACAGCTTTTCAT
CAGCAGAAGTGGCCGTCAAAGTCTGCA
ACCTAGTACTGCAAGAGAATTTTCCCACCGTAGCCAGCTATAACATAACGGA
TGAGTATGATGCCTATCTTGATATGGTG
GACGGAGCATCCTGCTGTTTAGATACTGCCACCTTTTGCCCAGCCAAATTAAG
GAGCTTTCCAAAGAAGCACAGTTATTT
GCGGCCTGAGATACGATCAGCAGTGCCATCACCGATTCAAAACACGCTCCAG
AATGTACTAGCAGCAGCCACGAAACGGA
ATTGCAATGTCACTCAAATGAGGGAACTTCCAGTGTTGGATTCAGCTGCCTTC
AACGTGGAGTGTTTCAAAAAGTACGCC
TGTAACGATGAGTACTGGGACTTCTACAAGACAAACCCGATAAGACTCACCG
CAGAAAATGTTACTCAGTATGTTACTAA

-continued

Sequence for FL-91

GTTAAAGGGACCCAAAGCAGCTGCCCTTTTTGCGAAAACGCATAACTTACAG

CCATTGCATGAGATACCAATGGATAGAT

TCGTGATGGACCTTAAACGGGATGTCAAGGTTACACCCGGGACAAAACATAC

TGAAGAAAGACCAAAAGTTCAGGTGATA

CAGGCAGCTGATCCACTTGCAACCGCCTACCTATGTGGTATACATCGAGAGC

TTGTGCGCAGGTTGAACGCAGTGCTGCT

ACCGAACATCCACACTTTGTTTGACATGTCTGCAGAAGATTTTGATGCTATCA

TTGCCGAACACTTTCAATTCGGCGACG

CGGTGTTAGAGACAGACATAGCTTCTTTTGATAAAAGCGAGGACGATGCTAT

CGCCATGTCTGCTCTAATGATTCTTGAA

GACCTAGGAGTTGATCAGGCACTGTTAAACCTAATTGAAGCAGCCTTTGGGA

ACATAACATCTGTGCACTTACCAACAGG

CACCCGATTTAAGTTCGGGGCAATGATGAAATCCGGGATGTTTTTGACACTCT

TTATTAATACTGTTGTCAATATCATGA

TCGCTAGCCGCGTGCTCCGCGAGCGGTTGACCACTTCCCCCTGCGCAGCATTT

ATCGGCGACGACAACATCGTGAAAGGG

GTTACATCTGACGCGCTGATGGCAGAGCGGTGCGCCACGTGGTTGAACATGG

AAGTGAAGATCATCGATGCAGTAGTCGG

AGTAAAGGCACCGTACTTTTGCGGAGGGTTCATCGTAGTCGATCAGATCACA

GGAACTGCGTGCAGAGTCGCCGACCCCC

TGAAGAGACTGTTTAAGCTAGGTAAGCCGCTTCCACTGGACGATGACCAAGA

CGTCGACAGGCGCAGAGCTCTGCATGAT

GAAGCGGCACGTTGGAACAGAATTGGCATCACTGAAGAGCTGGTGAAAGCA

GTTGAATCACGCTACGAGGTGAACTACGT

GTCACTAATCATCACAGCGTTGACTACATTAGCATCTTCAGTTAGCAACTTTA

AACACATAAGAGGTCACCCCATAACCC

TCTACGGCTGACCTAAATAGGTTGTGCATTAGTACCTAACCTATTTATATTAT

ATTGCTATCTAAATATCAGAGATGTTC

CCATACCCTACACTTAACTACCCGCCTATGGCGCCGATTAACCCGATGGCCTA

CCGGGATCCTAATCCGCCTAGGCGCAG

GTGGCGGCCCTTTAGGCCACCACTTGCAGCTCAAATTGAGGACCTGAGACGT

TCCATTGCTAACCTGACTTTGAAACAAC

GAGCACCTAACCCTCCAGCAGGACCGCCCGCCAAACGCAAGAAGCCTGCGCC

CAAGCCTAAGCCTGCGCAGGCGAAAAAG

AAGCGACCACCACCACCTGCCAAGAAACAAAAACGTAAACCTAAACCAGGC

AAACGACAGCGAATGTGTATGAAGCTAGA

GTCAGATAAAACGTTTCCGATCATGTTGAACGGACAGGTGAATGGTTACGCG

TGCGTCGTGGGTGGACGAGTGTTTAAAC

-continued

Sequence for FL-91

```
CGCTGCACGTAGAAGGCAGAATAGACAACGAGCAACTGGCCGCTATCAAGC
TGAAGAAGGCCAGCATATATGACCTTGAG
TACGGTGATGTGCCACAATGCATGAAATCAGATACCCTCCAGTACACCAGTG
ACAAGCCTCCTGGCTTTTATAACTGGCA
TCATGGAGCTGTGCAGTATGAGAACAACAGGTTCACCGTACCACGAGGGGTC
GGTGGAAAGGGCGACAGCGGGAGACCTA
TTCTTGACAACAAAGGTAGAGTCGTCGCAATTGTCCTGGGTGGAGTCAACGA
AGGATCCAGGACGGCTCTATCAGTGGTG
ACATGGAACCAAAAGGGGGTTACAGTCAAAGATACACCAGAGGGGTCAGAG
CCATGGTCGCTCGCCACTGTTATGTGCGT
CCTGGCCAATATCACGTTTCCATGTGATCAACCACCCTGCATGCCATGCTGTT
ATGAAAAGAATCCACACGAAACACTCA
CCATGCTGGAACAGAATTACGACAGCCGAGCCTATGATCAGCTGCTCGATGC
CGCTGTGAAATGTAATGCTAGGAGAACC
AGGAGAGATTTGGACACTCATTTCACCCAGTATAAGTTGGCACGCCCGTATA
TTGCTGATTGCCCTAACTGTGGGCATAG
TCGGTGCGACAGCCCTATAGCTATAGAAGAAGTCAGAGGGGATGCGCATGCA
GGAGTCATCCGCATCCAGACATCAGCTA
TGTTCGGTCTGAAGACGGATGGAGTCGATTTGGCCTACATGAGTTTCATGAAC
GGCAAAACGCAGAAATCAATAAAGATC
GACAACCTGCATGTGCGCACCTCAGCCCCTTGTTCCCTCGTGTCGCACCACGG
CTATTACATCTTGGCTCAATGCCCACC
AGGGGACACGGTTACAGTTGGGTTTCACGACGGGCCTAACCGCCATACGTGC
ACAGTTGCCCATAAGGTAGAATTCAGGC
CAGTGGGTAGAGAGAAATACCGTCACCCACCTGAACATGGAGTTGAACTACC
GTGTAACCGTTACACTCACAAGCGTGCA
GACCAAGGACACTATGTTGAGATGCATCAACCAGGGCTAGTTGCCGACCACT
CTCTCCTTAGCATCCACAGTGCCAAGGT
GAAAATTACGGTACCGAGCGGCGCCCAAGTGAAATACTACTGCAAGTGTCCA
GATGTACGAGAGGGAATTACCAGCAGCG
ACCATACAACCACCTGCACGGATGTCAAACAATGCAGGGCTTACCTGATTGA
CAACAAGAAATGGGTGTACAACTCTGGA
AGACTGCCTCGAGGAGAGGGCGACACTTTTAAAGGAAAACTTCATGTGCCCT
TTGTGCCTGTTAAGGCCAAGTGCATCGC
CACGCTGGCACCGGAGCCTCTAGTTGAGCACAAACACCGCACCCTGATTTTA
CACCTGCACCCGGACCATCCGACCTTGC
TGACGACCAGGTCACTTGGAAGTGATGCAAATCCAACTCGACAATGGATTGA
GCGACCAACAACTGTCAATTTCACAGTC
```

-continued

Sequence for FL-91

ACCGGAGAAGGGTTGGAGTATACCTGGGGAAACCATCCACCAAAAAGAGTA

TGGGCTCAAGAGTCAGGAGAAGGGAACCC

ACATGGATGGCCGCACGAAGTGGTAGTCTATTACTACAACAGATACCCGTTA

ACCACAATTATCGGGTTATGCACCTGTG

TGGCTATCATCATGGTCTCTTGTGTCACATCCGTGTGGCTCCTTTGCAGGACT

CGCAATCTTTGCATAACCCCGTATAAA

CTAGCCCCGAACGCTCAAGTCCCAATACTCCTGGCGTTACTTTGCTGCATTAA

GCCGACGAGGGCAGACGACACCTTGCA

AGTGCTGAATTATCTGTGGAACAACAATCAAAACTTTTTCTGGATGCAGACG

CTTATCCCACTTGCAGCGCTTATCGTAT

GCATGCGCATGCTGCGCTGCTTATTTTGCTGTGGGCCGGCTTTTTTACTTGTCT

GCGGCGCCTTGGGCGCCGCAGCGTAC

GAACACACAGCAGTGATGCCGAACAAGGTGGGGATCCCGTATAAAGCTTTAG

TCGAACGCCCAGGTTATGCACCCGTTCA

TCTACAGATACAGCTGGTTAATACCAGGATAATTCCATCAACTAACCTGGAG

TACATCACCTGCAAGTACAAGACAAAAG

TGCCGTCTCCAGTAGTGAAATGCTGCGGTGCCACTCAATGTACCTCCAAACCC

CATCCTGACTATCAGTGTCAGGTGTTT

ACAGGTGTTTACCCATTCATGTGGGGAGGAGCCTACTGCTTCTGCGACACCG

AAAACACCCAGATGAGCGAGGCGTATGT

AGAGCGCTCGGAAGAGTGCTCTATCGACCACGCAAAAGCTTATAAAGTACAC

ACAGGCACTGTTCAGGCAATGGTGAACA

TAACTTATGGGAGCGTCAGCTGGAGATCTGCAGATGTCTACGTCAATGGTGA

AACTCCCGCGAAAATAGGAGATGCCAAA

CTCATCATAGGTCCACTGTCATCTGCGTGGTCCCCATTCGATAACAAGGTGGT

GGTTTATGGGCATGAAGTGTATAATTA

CGACTTTCCTGAGTACGGCACCGGCAAAGCAGGCTCTTTTGGAGACCTGCAA

TCACGCACATCAACCAGCAACGATCTGT

ACGCAAACACCAACTTGAAGCTACAACGACCCCAGGCTGGTATCGTGCACAC

ACCTTTCACCCAGGCGCCCTCTGGCTTC

GAACGATGGAAAAGGGACAAAGGGGCACCGTTGAACGACGTAGCCCCGTTT

GGCTGTTCGATTGCCCTGGAGCCGCTCCG

TGCAGAAAATTGTGCAGTGGGAAGCATCCCTATATCTATAGATATACCCGAT

GCGGCTTTCACTAGAATATCTGAAACAC

CGACAGTCTCAGACCTGGAATGCAAAATTACGGAGTGTACTTATGCCTCCGA

TTTCGGTGGTATAGCCACCGTTGCCTAC

AAATCCAGTAAAGCAGGAAACTGTCCAATTCATTCTCCATCAGGTGTTGCAG

TTATTAAAGAGAATGACGTCACCCTTGC

-continued

Sequence for FL-91

TGAGAGCGGATCATTTACATTCCACTTCTCCACTGCAAACATCCATCCTGCTT

TTAAGCTGCAGGTCTGCACCAGTGCAG

TTACCTGCAAAGGAGATTGCAAGCCACCGAAAGATCATATCGTCGATTATCC

AGCACAACATACCGAATCCTTTACGTCG

GCGATATCCGCCACCGCGTGGTCGTGGCTAAAAGTGCTGGTAGGAGGAACAT

CAGCATTTATTGTTCTGGGGCTTATTGC

TACAGCAGTGGTTGCCCTAGTTCTGTTCTTCCATAGACATTAACATCTTGTCA

ACCACATAACACTACAGGCAGTGTATA

AGGCTGTCTTACTAAACACTAAATTCACCCTAGTTCGATGTACTTCCGAGCTA

TGGTGACGGTGGTGCATAATGCCGCCG

ATGCAGTGCATAAGGCTGCTATATTACCAAATTATAACACTAAGGGCAGTGC

ATAATGCTGCTCCTAAGTAATTTTATAC

ACACTTTATAATCAGGCATAATTGCCGTATATACAATTACACTACAGGTAATA

TACTGCCTCTTATAAACACTACAGGCA

GCGCATAATGCTGTCTTTTATATCAATTTACAAAATCATATTAATTTTTCTTTT

ATGTTTTTATTTTGTTTTTAATATTT

CAAAAAAAAAAAAAAAAAAAAAGCGGCGCCTTCGAAGGGCGAAATTCTGC

AGATATTCATCACACTGGCGGCCGcTCGA

GCATGCATCTAGAGG

What is claimed is:

1. An isolated and purified DNA of SEQ ID NO. 1 comprising an FL91-4679 eastern equine encephalitis (EEE) virus cDNA fragment coding for infectious eastern equine encephalitis virus RNA genome, wherein said cDNA fragment coding for infectious eastern equine encephalitis virus RNA genome contains a deletion of the furin cleavage site and a suppressor mutation(s) in E1, E2 and/or E3.

2. The DNA according to claim 1, wherein said EEE cDNA fragment is operably linked to a promoter such that said cDNA is transcribed.

3. An isolated and purified attenuated EEE virus RNA transcript encoded by the cDNA fragment of claim 1.

4. Isolated and purified attenuated EEE virus particles containing an RNA transcript according to claim 1.

5. A live attenuated eastern equine encephalitis (EEE) virus vaccine comprising attenuated EEE virus according to claim 4.

6. A pharmaceutical formulation comprising attenuated EEE virus particles according to claim 4 in an effective immunogenic amount in a pharmaceutically acceptable carrier.

7. An inactivated EEE vaccine comprising attenuated EEE according to claim 4 wherein said attenuated EEE is inactivated.

8. A live attenuated eastern equine encephalitis virus vaccine comprising an isolated and purified DNA comprising one or more of the candidates selected from the group consisting of (1) a DNA comprising an eastern equine encephalitis virus cDNA fragment coding for infectious FL91-4679 eastern equine encephalitis virus RNA genome, wherein said cDNA fragment contains a deletion in the furin cleavage site and one or more suppressor mutations in E1, E2 and/or E3, (2) a DNA comprising an FL91-4679 eastern equine encephalitis virus cDNA fragment coding for infectious eastern equine encephalitis virus genome, wherein said cDNA fragment contains a partial deletion of the furin cleavage site and one or more suppressor mutations in E1, E2 and/or E3, and (3) a DNA comprising an FL91-4679 eastern equine encephalitis virus cDNA fragment coding for infectious eastern equine encephalitis virus genome, wherein said cDNA fragment contains a four amino acid deletion from codons 21-24 of the E3 gene.

9. A live attenuated eastern equine encephalitis virus vaccine comprising—one or more of an isolated and purified DNA of SEQ ID NO. 1 of eastern equine encephalitis virus cDNA fragment coding for infectious eastern equine encephalitis virus genome, wherein said one or more DNA is selected from the group consisting of: (1) said DNA, wherein said cDNA contains a deletion of the furin cleavage site and a suppressor mutation of a substitution of an aspartic acid at codon 174 of E2 gene to an alanine, (2) said DNA, wherein said cDNA contains a deletion of the furin cleavage site and a suppressor mutation of a substitution of a lysine at codon 186 of E2 gene to an asparagines, (3) said DNA, wherein said cDNA contains a deletion of the furin cleavage site and a suppressor mutation of a substitution of an isoleucine at codon 116 of E1 gene to a threonine, (4) said DNA, wherein said cDNA contains a deletion of the furin cleavage site and a suppressor mutation of a substitution of a histidine at codon 82 of E2 gene to an arginine, (5) said DNA, wherein said cDNA contains a deletion of the furin cleavage site and a suppressor mutation of a substitution of an asparagine at codon 230 of E2 gene to a serine, (6) said DNA, wherein said cDNA contains a deletion of the furin cleavage site and a suppressor mutation of a substitution of a proline at codon 303 of E2 gene to a glutamine, (7) said DNA, wherein said cDNA contains a deletion of the furin cleavage site and a suppressor mutation of a substitution of an isoleucine at codon 116 of E1 gene to an aspargagine, (8) said DNA, wherein said cDNA contains a deletion of the furin cleavage site and a suppressor mutation of a deletion of a histidine at codon 167 of E2 gene, (9) wherein said cDNA fragment contains a partial deletion of the furin cleavage site and a suppressor mutation of a substitution of a histidine at codon 82 of E2 gene to an arginine, (10) wherein said cDNA fragment contains a partial deletion of the furin cleavage site and a suppressor mutation of a deletion of a histidine at codon 167 of E2 gene, (11) wherein said cDNA fragment contains a partial deletion of the furin cleavage site and a suppressor mutation of a substitution of an arginine at codon 59 of E3 gene to a serine, (12) wherein said cDNA fragment contains a partial deletion of the furin cleavage site and a suppressor mutation of a substitution of an asparagine at codon 80 of E2 gene to an aspartic acid, and (13) wherein said cDNA fragment contains a four amino acid deletion from codons 21-24 in an E3 gene.

10. The vaccine of claim 7, wherein said vaccine comprises a pharmaceutically acceptable carrier.

11. An isolated and purified DNA of SEQ ID NO. 1 of eastern equine encephalitis (EEE) virus cDNA fragment coding for infectious eastern equine encephalitis virus RNA genome and containing a deletion of the furin cleavage site and a suppressor mutation, said suppressor mutation comprising:
   a substitution of aspartic acid at codon 174 in E2 protein to an alanine, said E2 protein recited in SEQ ID NO. 1.

12. An isolated and purified DNA of SEQ ID NO. 1 of eastern equine encephalitis (EEE) virus cDNA fragment coding for infectious eastern equine encephalitis virus RNA genome and containing a deletion of the furin cleavage site and a suppressor mutation, said suppressor mutation comprising:
   a substitution of lysine at codon 186 in E2 protein to an asparagine, said E2 protein recited in SEQ ID NO. 1.

13. An isolated and purified DNA of SEQ ID NO. 1 of eastern equine encephalitis (EEE) virus cDNA fragment coding for infectious eastern equine encephalitis virus RNA genome and containing a deletion of the furin cleavage site and a suppressor mutation, said suppressor mutation comprising:
   a substitution of isoleucine at codon 116 in E1 protein to a threonine, said E1 protein recited in SEQ ID NO. 1.

14. An isolated and purified DNA of SEQ ID NO. 1 of eastern equine encephalitis (EEE) virus cDNA fragment coding for infectious eastern equine encephalitis virus RNA genome and containing a deletion of the furin cleavage site and a suppressor mutation, said suppressor mutation comprising:
   a substitution of histidine at codon 82 in E2 protein to an arginine, said E2 protein recited in SEQ ID NO. 1.

15. An isolated and purified DNA of SEQ ID NO. 1 of eastern equine encephalitis (EEE) virus cDNA fragment coding for infectious eastern equine encephalitis virus RNA genome and containing a deletion of the furin cleavage site and a suppressor mutation, said suppressor mutation comprising:
   a substitution of an asparagine at codon 230 in E2 protein to a serine, said E2 protein recited in SEQ ID NO. 1.

16. An isolated and purified DNA of SEQ ID NO. 1 of eastern equine encephalitis (EEE) virus cDNA fragment coding for infectious eastern equine encephalitis virus RNA genome and containing a deletion of the furin cleavage site and a suppressor mutation, said suppressor mutation comprising:
   a substitution of proline at codon 303 in E2 protein to a glutamine, said E2 protein recited in SEQ ID NO. 1.

17. An isolated and purified DNA of SEQ ID NO. 1 of eastern equine encephalitis (EEE) virus cDNA fragment coding for infectious eastern equine encephalitis virus RNA genome and containing a deletion of the furin cleavage site and a suppressor mutation, said suppressor mutation comprising:
   a substitution of an isoleucine at codon 116 in E1 protein to an asparagine, said E1 protein recited in SEQ ID NO. 1.

18. An isolated and purified DNA of SEQ ID NO. 1 of eastern equine encephalitis (EEE) virus cDNA fragment coding for infectious eastern equine encephalitis virus RNA genome and containing a deletion of the furin cleavage site and a suppressor mutation, said suppressor mutation comprising:
   a deletion of the histidine at codon 167 in E2 protein, said E2 protein recited in SEQ ID NO. 1.

\* \* \* \* \*